(12) United States Patent
York et al.

(10) Patent No.: US 8,889,614 B2
(45) Date of Patent: Nov. 18, 2014

(54) ENCAPSULATES

(75) Inventors: David William York, Newcastle upon Tyne (GB); Johan Smets, Lubeek (BE); Susana Fernandez Prieto, Benicarlo-Castellon (ES); Zhibing Zhang, Birmingham (GB); Angel Fernandez-Gonzalez, Valladolid (ES)

(73) Assignee: The Procter & Gamble Company, Cincinnati, OH (US)

( * ) Notice: Subject to any disclaimer, the term of this patent is extended or adjusted under 35 U.S.C. 154(b) by 167 days.

(21) Appl. No.: 13/328,196

(22) Filed: Dec. 16, 2011

(65) Prior Publication Data
US 2012/0152268 A1 Jun. 21, 2012

(30) Foreign Application Priority Data

Dec. 21, 2010 (EP) .................................... 10196327

(51) Int. Cl.
| | |
|---|---|
| *A61K 8/11* | (2006.01) |
| *C11D 3/37* | (2006.01) |
| *B01J 13/16* | (2006.01) |
| *C11D 17/00* | (2006.01) |
| *C11D 3/50* | (2006.01) |
| *B01J 13/20* | (2006.01) |

(52) U.S. Cl.
CPC .......... *C11D 17/0039* (2013.01); *C11D 3/3719* (2013.01); *B01J 13/16* (2013.01); *C11D 3/3769* (2013.01); *A61K 2800/412* (2013.01); *C11D 3/505* (2013.01); *B01J 13/206* (2013.01)
USPC ........................................................ 512/4

(58) Field of Classification Search
USPC .......................................................... 512/4
See application file for complete search history.

(56) References Cited

U.S. PATENT DOCUMENTS

| | | |
|---|---|---|
| 3,575,882 A | 4/1971 | Vandegaer et al. |
| 4,430,243 A | 2/1984 | Bragg |
| 5,486,303 A | 1/1996 | Capeci et al. |
| 5,489,392 A | 2/1996 | Capeci et al. |
| 5,516,448 A | 5/1996 | Capeci et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |
| 5,597,936 A | 1/1997 | Perkins et al. |
| 5,691,297 A | 11/1997 | Nassano et al. |
| 5,879,584 A | 3/1999 | Bianchetti et al. |
| 6,225,464 B1 | 5/2001 | Hiler, II et al. |
| 6,306,812 B1 | 10/2001 | Perkins et al. |
| 6,326,348 B1 | 12/2001 | Vinson et al. |
| 7,169,741 B2 | 1/2007 | Barry et al. |
| 7,297,674 B2 | 11/2007 | Hines |
| 2002/0158356 A1 | 10/2002 | Argillier |
| 2005/0130864 A1 | 6/2005 | Ouwendijk-Vrijenhoek et al. |
| 2007/0207174 A1 * | 9/2007 | Pluyter et al. ................. 424/401 |

FOREIGN PATENT DOCUMENTS

| | | |
|---|---|---|
| EP | 1 640 063 A1 | 3/2006 |
| GB | 1091141 | * 11/1967 |
| WO | WO 00/32601 | 6/2000 |

OTHER PUBLICATIONS

International Search Report for International Application Serial No. PCT/IB2011/055861, mailed Apr. 10, 2012, 11 pages.
Extended European Search Report for Application No. 10196327.0-2114, mailed May 4, 2011, 6 pages.

* cited by examiner

*Primary Examiner* — John Hardee
(74) *Attorney, Agent, or Firm* — Gregory S. Darley-Emerson; Steven W. Miller

(57) ABSTRACT

Encapsulates, compositions, packaged products and displays comprising such encapsulates, and processes for making and using such encapsulates, compositions, packaged products and displays. Such compositions have improved deposition and retention properties that may impart improved benefit characteristics to a composition and/or situs.

13 Claims, No Drawings

ENCAPSULATES

FIELD OF INVENTION

The present application relates to encapsulates, compositions, products comprising such encapsulates, and processes for making and using such encapsulates.

BACKGROUND OF THE INVENTION

Perfumes are expensive and may be less effective when employed at high levels in compositions such as personal care compositions, cleaning compositions, and fabric care compositions. As a result, there is a desire to maximize the effectiveness of perfumes. One manner of achieving such objective is to improve the delivery efficiencies of the perfume. Unfortunately, it is difficult to improve the delivery efficiencies of perfumes as they may be lost due to their physical or chemical characteristics, they may be incompatible with other compositional components or the situs that is treated, or they may be lost during post application processes such as rinsing or drying.

One method of improving the delivery efficiency of perfumes is to encapsulate them so that the perfume is only released, for example by fracturing the shell of the encapsulate, when the benefit agent is desired. However, current encapsulated perfumes that are encapsulated by polyamides leak perfume over time and current encapsulated perfumes, in general, do not fracture and release the perfume when desired—particularly in hard surface treatment applications. In short, current polyamide-based encapsulates do not provide the required delivery efficiency as they do not deliver perfume in quantity or at the time desired.

Accordingly, there is a need for a polyamide encapsulate that provides improved perfume delivery. Here, Applicants recognized that the source of the leakage problem and delivery timing was that previous polyamide encapsulates shells were not sufficiently compact. While not being bound by theory, Applicants believe that the aforementioned lack of compaction is due to the use of only one water miscible monomer and one water immiscible, organic monomer in the current art polyamide encapsulates and the manner in which such monomers are processed to form such encapsulates. Furthermore, Applicants recognized that size and selection of the monomers used to construct the encapsulates shell is important in obtaining the necessary packing density of the shell. While not being bound by theory, applicants believe that the encapsulates that are disclosed herein have the correct packing density and thus meet the aforementioned need as such encapsulates are tailored such that they have the desired leakage profile and release profile.

SUMMARY OF THE INVENTION

Encapsulates, compositions, packaged products and displays comprising such encapsulates, and processes for making and using such encapsulates, compositions, packaged products and displays are disclosed. Such encapsulates comprise a core comprising a perfume and a shell that at least partially surrounds said core, such encapsulates may optionally comprise a parametric balancing agent.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning and/or treatment composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations thereof.

As used herein, the articles "a" and "an" when used in a claim, are understood to mean one or more of what is claimed or described.

As used herein, the terms "include", "includes" and "including" are meant to be synonymous with the phrase "including but not limited to".

As used herein, the term "solid" means granular, powder, bar and tablet product forms.

As used herein, the term "situs" includes paper products, fabrics, garments, hard surfaces, hair and skin.

As used herein, a "parametric balancing agent" is a material that can be employed to alter one or more of the following properties of an encapsulate and/or the encapsulate's core material: density, vapor pressure and/or ClogP. When a parametric balancing agent is used to alter the vapor pressure of an encapsulate and/or the encapsulate's core material, the boiling of such encapsulate and/or the encapsulate's core material is inherently altered.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Encapsulates and Compositions Comprising Same

The time period for determining the leakage profile of an encapsulate may include the time the encapsulate is in product and the time such product is in use. The satisfactory delivery of the content of an encapsulate requires optimum capsule mechanical properties as if the capsule is too strong, it never releases its content and if a capsule is too weak, it breaks to soon thus releasing it contents prematurely. In addition, capsule mechanical properties can be compromised by various factors such as prolonged exposure at high temperature and/or low pH and thus the leakage profile of a capsule with optimal mechanical properties can be compromised.

Applicants recognized that the source of the aforementioned leakage problem is not only due to the amount of water miscible and water immiscible monomers in the shell/wall of the encapsulate but is also due to the low packing density of the molecules in the shell/wall of the encapsulate. Applicants recognized that the right balance of properties (stability in product and release during application) can be achieved by combining two or more water miscible monomers and two or more water immiscible monomers. Such, encapsulates and compositions comprising such encapsulates are disclosed below.

A population of encapsulates, at least 80%, at least 85% of the encapsulates, or even at least 90% of the encapsulates comprising a shell and a core, said shell comprising a polyamide polymer that forms a wall that encapsulates said core, said core comprising a perfume composition, said perfume composition comprising perfume raw materials having a ClogP of from about 2.0 to about 4.5, or even from about 2.5 to about 4.25, said encapsulate having a diameter of from about 1 µm to about 100 µm, from about 5 µm to about 60 µm, or even from about 5 µm to about 40 µm, said encapsulate having a fracture strength from about 0.1 MPa to about 5 MPa, from about 0.5 MPa to 4 MPa, or even from about 1 MPa to about 4 MPa is disclosed.

In one aspect of said encapsulate, said polyamide polymer may comprise at least one water miscible monomer and one water immiscible organic monomer.

In one aspect of said encapsulate, said water miscible monomer may comprise a material selected from the group consisting of a diamine, a triamine and mixtures thereof. In one aspect, said diamines and triamines may be selected from the group consisting of diethylene triamine, hexamethylene diamine, ethylene diamine and mixtures thereof.

In one aspect of said encapsulate, said water immiscible organic monomer may be selected from the group consisting of diacyl chlorides, triacyl chlorides and mixtures thereof. In one aspect, said diacyl chlorides may be selected from the group consisting of sebacoyl dichloride, adipoyl dichloride, and mixtures thereof and said triacyl chlorides may be selected from the group consisting of teraphthaloyl chloride, trimesoyl chloride, acetyl chloride, benzoyl chloride, 1,3,5-benzentricarbonyl chloride, and mixtures thereof.

In one aspect of said encapsulate, said polyamide polymer may comprise two or more water miscible monomers.

In one aspect of said encapsulate, said polyamide polymer may comprise two or more water immiscible organic monomers.

In one aspect of said encapsulate, said encapsulate's core may comprise a perfume composition selected from the group consisting of:
  a) a perfume composition having a ClogP of less than 4.5 to about 2, less than 4.25 to about 2.2, less than 4.0 to about 2.5 or even less than 3.75 to about 2.6;
  b) a perfume composition comprising, based on total perfume composition weight, at least 60% or even at least 70% perfume materials having a ClogP of less than 4.0 to about 2.0;
  c) a perfume composition comprising, based on total perfume composition weight, at least 35%, at least 50% or even at least 60% perfume materials having a ClogP of less than 3.5 to about 2;
  d) a perfume composition comprising, based on total perfume composition weight, at least 40% perfume materials having a ClogP of less than 4.0 to about 2.0 or even less than 3.5 to about 2.0 and at least 1% perfume materials having a ClogP of less than 2.0 to about 1.0;
  e) a perfume composition comprising, based on total perfume composition weight, at least 40% perfume materials having a ClogP of less than 4.0 to about 2 or even less than 3.5 to about 2.0 and at least 15% perfume materials having a ClogP of less than 3.0 to about 1.5;
  f) a perfume composition comprising, based on total perfume composition weight, at least 1% or even at least 2.0% of a butanoate ester and at least 1% of a pentanoate ester;
  g) a perfume composition comprising, based on total perfume composition weight, at least 2.0% or even at least 3.0% of an ester comprising an allyl moiety and at least 10%, at least 25% or even at least 30% of another perfume comprising an ester moiety;
  h) a perfume composition comprising, based on total perfume composition weight, at least 1.0% or even at least 5.0% of an aldehyde comprising an alkyl chain moiety;
  i) a perfume composition comprising, based on total perfume composition weight, at least 2.0% of a butanoate ester;
  j) a perfume composition comprising, based on total perfume composition weight, at least 1.0% of a pentanoate ester;
  k) a perfume composition comprising, based on total perfume composition weight, at least 3.0% of an ester comprising an allyl moiety and at least 1.0% of an aldehyde comprising an alkyl chain moiety;
  l) a perfume composition comprising, based on total perfume composition weight, at least 25% of a perfume comprising an ester moiety and at least 1.0% of an aldehyde comprising an alkyl chain moiety; and m) a perfume composition comprising, based on total perfume composition weight, from about 0.5% to about 50%, from about 1.0% to about 40%, or even from about 5.0% to about 30% of a parametric balancing agent.

with the proviso that the perfume composition does not contain alcohols and/or primary amine perfume raw materials.

In one aspect of said encapsulate, said encapsulate may have a leakage index of from about 0 to about 0.35, from about 0.02 to about 0.20, or even from about 0.05 to about 0.15.

In one aspect of said encapsulate, said encapsulate may have a core to shell mass ratio of from about 75:25 to about 95:5, or even from about 80:20 to about 90:10.

In one aspect a composition, that may have any of the parameters disclosed herein and may comprise any of the encapsulates described herein and an adjunct material, is disclosed.

In one aspect a consumer product comprising, based on total consumer product weight, from about 0.01% to about 80%, from about 0.1% to about 50%, from about 1.0% to about 25% or from about 1.0% to about 10% of the encapsulates disclosed herein, is disclosed.

In one aspect of said consumer product, at least 75%, at least 85% or even at least 90% of said encapsulates may have an encapsulate wall thickness of from about 50 nm to about 500 nm, from about 70 nm to about 450 nm, or even from about 120 nm to about 370 nm.

In one aspect of said consumer product, for said population of encapsulates, said encapsulates may have a percentage of free perfume composition of less than 10%.

Suitable Perfume Raw Materials

Perfumes that provide improved perfume performance under high soil conditions and in cold water may comprise Perfume Raw Materials as given in Table 1 below.

TABLE 1

Useful Perfume Raw Materials

| Item | Common Name | IUPAC Name |
|---|---|---|
| 1 | Methyl 2-methyl butyrate | methyl 2-methylbutanoate |
| 2 | Isopropyl 2-methyl butyrate | propan-2-yl 2-methylbutanoate |
| 3 | Ethyl-2 Methyl Butyrate | ethyl 2-methylbutanoate |
| 4 | Ethyl-2 Methyl Pentanoate | ethyl 2-methylpentanoate |
| 5 | Ethyl heptanoate | ethyl heptanoate |
| 6 | Ethyl octanoate | Ethyl octanoate |
| 7 | isobutyl hexanoate | 2-methylpropyl hexanoate |
| 8 | Amyl butyrate | pentyl butanoate |
| 9 | Amyl heptanoate | Pentyl heptanoate |
| 10 | Isoamyl isobutyrate | 3-methylbutyl 2-methylpropanoate |
| 11 | Hexyl acetate | hexyl acetate |
| 12 | hexyl butyrate | hexyl butanoate |
| 13 | hexyl isobutyrate | hexyl 2-methylpropanoate |
| 14 | hexyl isovalerate | hexyl 3-methylbutanoate |
| 15 | hexyl propionate | hexyl propanoate |
| 16 | Ethyl 2-cyclohexyl propanoate | ethyl 2-cyclohexylpropanoate |
| 17 | Ethyl 3,5,5-trimethyl hexanoate | ethyl 3,5,5-trimethylhexanoate |
| 18 | glyceryl 5-hydroxydecanoate | 2,3-dihydroxypropyl 5-hydroxydecanoate |
| 19 | Prenyl acetate | 3-methyl 2-butenyl acetate |
| 20 | 3-methyl 2-butenyl acetate | 3-methyl 2-butenyl acetate |
| 21 | methyl 3-nonenoate | methyl non-3-enoate |
| 22 | Ethyl (E)-dec-4-enoate | Ethyl (E)-dec-4-enoate |
| 23 | Ethyl (E)-oct-2-enoate | Ethyl (E)-oct-2-enoate |
| 24 | Ethyl 2,4-decadienoate | ethyl (2E,4Z)-deca-2,4-dienoate |
| 25 | Ethyl 3-octenoate | ethyl (E)-oct-3-enoate |
| 26 | Citronellyl acetate | 3,7-dimethyloct-6-enyl acetate |
| 27 | Ethyl trans-2-decenoate | ethyl (E)-dec-2-enoate |
| 28 | 2-hexen-1-yl isovalerate | [(E)-hex-2-enyl] acetate |
| 29 | 2-hexen-1-yl propionate | [(E)-hex-2-enyl] propanoate |
| 30 | 2-hexen-1-yl valerate | [(E)-hex-2-enyl] pentanoate |
| 31 | 3-hexen-1-yl (E)-2-hexenoate | [(Z)-hex-3-enyl] (E)-hex-2-enoate |
| 32 | 3-Hexen-1-yl 2-methyl butyrate | [(Z)-hex-3-enyl] 2-methylbutanoate |
| 33 | 3-hexen-1-yl acetate | [(Z)-hex-3-enyl] acetate |
| 34 | 3-hexen-1-yl benzoate | [(Z)-hex-3-enyl] benzoate |
| 35 | 3-hexen-1-yl formate | [(Z)-hex-3-enyl] formate |
| 36 | 3-hexen-1-yl tiglate | [(Z)-hex-3-enyl] (Z)-2-methylbut-2-enoate |
| 37 | 2-methyl butyl 2-methyl butyrate | 2-methylbutyl 2-methylbutanoate |
| 38 | Butyl isovalerate | butyl 3-methylbutanoate |
| 39 | Geranyl acetate | [(2E)-3,7-dimethylocta-2,6-dienyl] acetate |
| 40 | Geranyl butyrate | [(2E)-3,7-dimethylocta-2,6-dienyl] butanoate |
| 41 | Geranyl isovalerate | [(3E)-3,7-dimethylocta-3,6-dienyl] 3-methylbutanoate |
| 42 | Geranyl propionate | [(2E)-3,7-dimethylocta-2,6-dienyl] propanoate |
| 43 | Allyl cyclohexane acetate | prop-2-enyl 2-cyclohexylacetate |
| 44 | Allyl Cyclohexyl Propionate | prop-2-enyl 3-cyclohexylpropanoate |
| 45 | allyl cyclohexyl valerate | prop-2-enyl 5-cyclohexylpentanoate |
| 46 | benzyl octanoate | benzyl octanoate |
| 47 | Cocolactone | 6-pentyl-5,6-dihydropyran-2-one |
| 48 | coconut decanone | 8-methyl-1-oxaspiro(4.5)decan-2-one |
| 49 | gamma undecalactone | 5-heptyloxolan-2-one |
| 50 | gamma-decalactone | 5-hexyloxolan-2-one |
| 51 | gamma-dodecalactone | 5-octyloxolan-2-one |
| 52 | jasmin lactone | 6-[(E)-pent-2-enyl]oxan-2-one |

TABLE 1-continued

Useful Perfume Raw Materials

| Item | Common Name | IUPAC Name |
|---|---|---|
| 53 | Jasmolactone | 5-[(Z)-hex-3-enyl]oxolan-2-one |
| 54 | Nonalactone | 6-butyloxan-2-one |
| 55 | 6-acetoxydihydrotheaspirane | [2a,5a(S*)]-2,6,10,10-tetramethyl-1-oxaspiro[4.5]decan-6-yl acetate |
| 56 | Phenoxyethyl isobutyrate | 2-(phenoxy)ethyl 2-methylpropanoate |
| 57 | Pivacyclene | |
| 58 | Verdox | (2-tert-butylcyclohexyl) acetate |
| 59 | cyclobutanate | 3a,4,5,6,7,7a-hexahydro-4,7-methano-1g-inden-5(or 6)-yl butyrate |
| 60 | Dimethyl Anthranilate | methyl 2-methylaminobenzoate |
| 61 | Methyl Antranilate | methyl 2-aminobenzoate |
| 62 | Octyl Aldehyde | Octanal |
| 63 | Nonanal | Nonanal |
| 64 | Decyl aldehyde | Decanal |
| 65 | Lauric Aldehyde | Dodecanal |
| 66 | Methyl Nonyl Acetaldehyde | 2-methyl undecanal |
| 67 | Methyl Octyl Acetaldehyde | 2-methyl decanal |
| 68 | 2,4-Hexadienal | (2E,4E)-hexa-2,4-dienal |
| 69 | Intreleven Aldehyde | undec-10-enal |
| 70 | Decen-1-al | (E)-dec-2-enal |
| 71 | Nonen-1-al | (E)-2-nonen-1-al |
| 72 | Adoxal | 2,6,10-trimethylundec-9-enal |
| 73 | Geraldehyde | (4Z)-5,9-dimethyldeca-4,8-dienal |
| 74 | Iso cyclo citral | 2,4,6-trimethylcyclohex-3-ene-1-carbaldehyde |
| 75 | d-limonene mainly | 1-methyl-4-prop-1-en-2-yl-cyclohexene |
| 76 | Ligustral | 2,4-dimethylcyclohex-3-ene-1-carbaldehyde |
| 77 | Myrac aldehyde | 4-(4-methylpent-3-enyl)cyclohex-3-ene-1-carbaldehyde |
| 78 | Tridecenal | tridec-2-enal |
| 79 | Triplal | 2,4-dimethyl-3-cyclohexene-1-carboxaldehyde |
| 80 | Vertoliff | 1,2-dimethylcyclohex-3-ene-1-carbaldehyde |
| 81 | Cyclal C | 2,4-dimethylcyclohex-3-ene-1-carbaldehyde |
| 82 | Anisic aldehyde | 4-methoxybenzaldehyde |
| 83 | Helional | 3-(1,3-benzodioxol-5-yl)-2-methylpropanal |
| 84 | Heliotropin | 1,3-benzodioxole-5-carbaldehyde |
| 85 | Neocaspirene | |
| 86 | Beta Naphthol Ethyl Ether | 2-ethoxynaphtalene |
| 87 | Beta Naphthol Methyl Ether | 2-methoxynaphtalene |
| 88 | hyacinth ether | 2-cyclohexyloxyethylbenzene |
| 89 | 2-heptyl cyclopentanone (fleuramone) | 2-heptylcyclopentan-1-one |
| 90 | menthone-8-thioacetate | O-[2-[(1S)-4-methyl-2-oxocyclohexyl]propan-2-yl] ethanethioate |
| 91 | Nectaryl | 2-[2-(4-methyl-1-cyclohex-3-enyl)propyl]cyclopentan-1-one |
| 92 | Phenyl Naphthyl Ketone | naphthalen-2-yl-phenylmethanone |
| 93 | decen-1-yl cyclopentanone | 2-[(2E)-3,7-dimethylocta-2,6-dienyl]cyclopentan-1-one |
| 94 | fruity cyclopentanone (veloutone) | 2,2,5-trimethyl-5-pentylcyclopentan-1-one |
| 96 | Grapefruit Mercaptan | 2-(4-methyl-1-cyclohex-3-enyl)propane-2-thiol |
| 97 | Buccoxime | N-(1,5-dimethyl-8-bicyclo [3.2.1] octanylidene)hydroxylamine |
| 98 | Labienoxime | 2,4,4,7-Tetramethyl-6,8-nonadiene-3-one oxime |
| 101 | Diethyl maleate | diethyl but-2-enedioate |
| 102 | Ethyl Acetoacetate | ethyl 3-oxobutanoate |
| 103 | frutonile | 2-Methyldecanenitrile |
| 104 | Methyl dioxolan | ethyl 2-(2-methyl-1,3-dioxolan-2-yl)acetate |
| 105 | Cetalox | 3a,6,6,9a-tetramethyl-2,4,5,5a,7,8,9,9b-octahydro-1H-benzo[e][1]benzofuran |
| 107 | Delta-damascone | (E)-1-(2,6,6-trimethyl-1-cyclohex-3-enyl)but-2-en-1-one |
| 109 | Flor acetate | |
| 110 | Ionone gamma methyl | (E)-3-methyl-4-(2,6,6-trimethyl-1-cyclohex-2-enyl)but-3-en-2-one |
| 113 | Violiff | [(4Z)-1-cyclooct-4-enyl] methyl carbonate |
| 114 | Cymal | 3-(4-propan-2-ylphenyl)butanal |
| 115 | Bourgeonal | 3-(4-tert-butylphenyl)propanal |

Suitable Parametric Balancing Agents

In one aspect, the encapsulates disclosed herein may comprise a parametric balancing agent. In one aspect, at least a portion of said parametric balancing agent is contained in said encapsulate's shell. In another aspect, said encapsulate's core may comprise at least a portion of said parametric balancing agent.

In one aspect, said parametric balancing agent may be a density balancing agent. Without being bound by theory, density balancing agents are materials that are able to balance the density of an encapsulate so that such encapsulate can be stably suspended in a fluid consumer good. In one aspect of said encapsulate, said encapsulate may have a settling velocity of less than about 1.5 cm/year, less than about 1.0 cm/year.

In another aspect of said encapsulate, said perfume composition may comprise one or more fluids and may have a density such that the density ratio of said encapsulate and at least one of said one or more fluids is from about 0.9:1 to about 1.1:1. Suitable density balancing agents include: brominated vegetable oil, Tint Ayd PC 9003 and those listed in U.S. patent application Ser. No. 29,035,365 A1.

For example, the densifying agents may be metal oxides selected from but not limited to titanium dioxide ($TiO_2$), zinc oxide (ZnO), $Fe_2O_3$, $CO_2O_3$, CoO, NiO, AgO, CuO, zicornium dioxide ($ZrO_2$), silica, and other metal oxides. They should have specific density of greater than unity. Oxides that can function both as densification agent and provide additional functional properties are particularly useful.

In one aspect, the density of the densifying agent is greater than 1. By adding densifying agents to the core, the density of the encapsulate can be independently adjusted to a desired level. Hydrophobically modified metal oxides are useful. Examples of metal oxides include, but are not limited to, Uvinul® TiO2, Z-COTE® HP1, T-lite™ SF. T-lite™ SF-S, T-lite™ MAX, and Z-COTE® MAX manufactured by BASF; Aerosil® R812, Aerosil® R972/R94 from Evonik; and Ti-Pure® R-700, and Ti-Select™ TS-6200 from Dupont.

The densifying agents may also be selected from organic compounds including brominated vegetable oil (BVO) and sucrose acetate isobutyrate. Such densifying agents are available from Eastman chemical (Kingsport, Tenn. 37662) under the trade name: Sustane SAIB, Sustane SAIB MCT, Sustane SAIB ET-10, Eastman SAIB-100, Eastman SAIB-90EA, and Eastman SAIB-90. For the purpose of densification, any substances that possesses a density of greater than 1 and does not significantly react with the fragrance may be used. Furthermore, a material that is odorless or does not interfere with the primary odor of the fragrance is particularly useful. The selection can be made based on the chemical and physical compatibility of the densification agent and that of the fragrance core.

The densification agents may also be selected from inert metallic particles or metallic compounds or metallic alloys since these materials normally posses density of greater than 1.0 and can be highly effective in providing the desired density. Examples are silver (Ag), zinc (Zn), iron (Fe), cobalt (Co), Nickel (Ni), and copper (Cu). Useful materials are those compatible with the fragrance core.

In the case of a solid densification agent, the material can be of any physical dimension and morphology compatible with the desired encapsulate characteristics (e.g., size). The core materials can be selected from materials with dimensions ranging from a few nanometers to microns. As far as the physical dimension is concerned, the upper and lower limit of the core densification agent will be ultimately determined by the physical dimension of the encapsulates. For example, if one is to prepare a 30 micron densified capsule, the maximum physical dimension of the densification agent is limited to 30 micron or less. It is possible that, for optimal performance, there might exist a relationship between the physical dimension of the capsule and that of the core densification agent. For example, a larger capsule may need a densification agent with a larger physical size for better breakage and release. This may be explainable if the capsules breakage is by protrusion force. Likewise, a smaller capsule may benefit from material with a smaller grain size.

The core materials may further be hollow, porous, mesoporous, nano-porous or completely filled. The core materials can also be of any regular or irregular shape including sphere, square, needles, fibers, and ellipsoids. The physical dimension of the core materials can range from nanoscaled to micro-sized materials. The densification agents in the core can have any dimension, as long as they can be encapsulated in the polyamide encapsulating shell and as long as the fragrance core remains liquid after the fragrance core is mixed with the densification agent.

Additional suitable density balancing agents include those listed in Table 2 below.

TABLE 2

Density Balancing Agents Useful For Balancing Encapsulates Having Cores With a Density of Less Than 1

| Item | CAS Number | Registry Name | Trade name | Specific Gravity 25° C. (g/cm³) |
|---|---|---|---|---|
| 1 | 116-66-5 | 1h-indene, 2,3-dihydro-1,1,3,3,5-pentamethyl-4,6-dinitro- | moskene | solid |
| 3 | 120-24-1 | benzeneacetic acid, 2-methoxy-4-(1-propenyl)phenyl ester | isoeugenyl phenylacetate | solid |
| 4 | 2530-10-1 | ethanone, 1-(2,5-dimethyl-3-thienyl)- | 3-acetyl-2,5-dimeththiiophene | 1.1783 |
| 5 | 16546-01-3 | oxiranecarboxylic acid, 3-(4-methoxyphenyl)-, ethyl ester | methoxy ethyl phenyl glycidate | solid |
| 6 | 144761-91-1 | benzoic acid, 2-[(1-hydroxy-3-phenylbutyl)amino]-, methyl ester | trifone | solid |
| 7 | 6951-08-2 | 1,3-benzodioxole-5-carboxylic acid, ethyl ester | ethyl piperonylate | 1.2430 |
| 9 | 100-09-4 | benzoic acid, 4-methoxy- | p-anisic acid | solid |
| 10 | 90-17-5 | benzenemethanol, .alpha.-(trichloromethyl)-, acetate | trichloromethyl phenyl carbinyl acetate | solid |
| 11 | 10031-96-6 | phenol, 2-methoxy-4-(2-propenyl)-, formate | eugenyl formate | solid |
| 12 | 531-26-0 | phenol, 2-methoxy-4-(2-propenyl)-, benzoate | eugenyl benzoate | solid |
| 13 | 5320-75-2 | 2-propen-1-ol, 3-phenyl-, benzoate | cinnamyl benzoate | solid |
| 14 | 122-27-0 | benzeneacetic acid, 3-methylphenyl ester | m-cresyl phenylacetate | solid |
| 15 | 145-39-1 | benzene, 1-(1,1-dimethylethyl)-3,4,5-trimethyl-2,6-dinitro- | musk tibetine | solid |

TABLE 2-continued

Density Balancing Agents Useful For Balancing Encapsulates Having Cores With a Density of Less Than 1

| Item | CAS Number | Registry Name | Trade name | Specific Gravity 25° C. (g/cm³) |
|---|---|---|---|---|
| 16 | 101-94-0 | benzeneacetic acid, 4-methylphenyl ester | p-tolyl phenylacetate | solid |
| 17 | 102-16-9 | benzeneacetic acid, phenylmethyl ester | benzyl phenylacetate | solid |
| 18 | 102-17-0 | benzeneacetic acid, (4-methoxyphenyl)methyl ester | anisyl phenylacetate | solid |
| 19 | 103-41-3 | 2-propenoic acid, 3-phenyl-, phenylmethyl ester | benzyl cinnamate | solid |
| 20 | 103-53-7 | 2-propenoic acid, 3-phenyl-, 2-phenylethyl ester | phenethyl cinnamate | solid |
| 21 | 10402-33-2 | benzeneacetic acid, 2-methoxy-4-(2-propenyl)phenyl ester | eugenyl phenylacetate | solid |
| 23 | 111753-60-7 | benzoic acid, 2-[[3-(1,3-benzodioxol-5-yl)-2-methylpropylidene]amino]-, methyl ester | corps oranger 2 | solid |
| 25 | 1132-21-4 | benzoic acid, 3,5-dimethoxy- | 3,5-dimethoxybenzoic acid | solid |
| 26 | 118-55-8 | benzoic acid, 2-hydroxy-, phenyl ester | phenyl salicylate | solid |
| 27 | 118-58-1 | benzoic acid, 2-hydroxy-, phenylmethyl ester | benzyl salicylate | solid |
| 28 | 118-61-6 | benzoic acid, 2-hydroxy-, ethyl ester | ethyl salicylate | solid |
| 29 | 119-36-8 | benzoic acid, 2-hydroxy-, methyl ester | methyl salicylate | solid |
| 30 | 134-20-3 | benzoic acid, 2-amino-, methyl ester | methyl anthranilate | 1.1873 |
| 31 | 119-53-9 | ethanone, 2-hydroxy-1,2-diphenyl- | benzoin | solid |
| 32 | 120-47-8 | benzoic acid, 4-hydroxy-, ethyl ester | ethyl 4-hydroxybenzoate | solid |
| 33 | 120-51-4 | benzoic acid, phenylmethyl ester | benzyl benzoate | 1.1308 |
| 35 | 120-75-2 | benzothiazole, 2-methyl- | 2-methylbenzothiazole | solid |
| 36 | 1210-35-1 | 5h-dibenzo[a,d]cyclohepten-5-one, 10,11-dihydro- | dibenzosuberenone | solid |
| 37 | 121-39-1 | oxiranecarboxylic acid, 3-phenyl-, ethyl ester | ethyl 3-phenylglycidate | solid |
| 38 | 121-98-2 | benzoic acid, 4-methoxy-, methyl ester | methyl p-anisate | solid |
| 39 | 122-69-0 | 2-propenoic acid, 3-phenyl-, 3-phenyl-2-propenyl ester | cinnamyl cinnamate | 1.1210 |
| 40 | 122760-84-3 | tricyclo[3.3.1.13,7]decan-2-ol, 4-methyl-8-methylene- | tricyclo[3.3.1.13,7]decan-2-ol, 4-methyl-8-methylene- | solid |
| 41 | 122760-85-4 | tricyclo[3.3.1.13,7]decan-2-ol, 4-methyl-8-methylene-, acetate | tricyclo[3.3.1.13,7]decan-2-ol, 4-methyl-8-methylene-, acetate | solid |
| 42 | 131-55-5 | methanone, bis(2,4-dihydroxyphenyl)- | benzophenone-2 | solid |
| 43 | 131-57-7 | methanone, (2-hydroxy-4-methoxyphenyl)phenyl- | oxybenzone | solid |
| 44 | 132-64-9 | dibenzofuran | 2,2'-biphenylene oxide | solid |
| 45 | 133-18-6 | benzoic acid, 2-amino-, 2-phenylethyl ester | phenethyl anthranilate | 1.1752 |
| 46 | 1333-52-4 | ethanone, 1-(naphthalenyl)- | 1-(naphthyl)ethan-1-one | solid |
| 47 | 13678-67-6 | furan, 2,2'-[thiobis(methylene)]bis- | 2,2'-(thiodimethylene)-difuran | solid |
| 48 | 139-45-7 | 1,2,3-propanetriol, tripropanoate | glyceryl tripropanoate | 1.1009 |
| 49 | 140-10-3 | 2-propenoic acid, 3-phenyl-, (e)- | trans-cinnamic acid | solid |
| 51 | 14173-25-2 | disulfide, methyl phenyl | methyl phenyl disulfide | 1.1776 |
| 53 | 14737-91-8 | 2-propenoic acid, 3-(2-methoxyphenyl)-, (z)- | cis-2-methoxycinnamic acid | solid |
| 54 | 148-24-3 | 8-quinolinol | 8-hydroxyquinoline | solid |
| 55 | 150-60-7 | disulfide, bis(phenylmethyl) | dibenzyl disulfide | solid |
| 56 | 19224-26-1 | 1,2-propanediol, dibenzoate | propylene glycol dibenzoate | 1.1686 |
| 57 | 2039-82-9 | benzene, 1-bromo-4-ethenyl- | 4-bromostyrene | 1.3931 |
| 58 | 2050-87-5 | trisulfide, di-2-propenyl | diallyl trisulfide | 1.1346 |
| 60 | 2257-09-2 | benzene, (2-isothiocyanatoethyl)- | phenethyl isothiocyanate | solid |
| 61 | 22717-57-3 | benzoic acid, 2-hydroxy-5-methyl-, methyl ester | methyl-5-methylsalicylate | solid |
| 62 | 23654-92-4 | 1,2,4-trithiolane, 3,5-dimethyl- | 3,5-dimethyl-1,2,4-trithiolane | 1.3018 |
| 63 | 23747-43-5 | propanoic acid, 2-(methyldithio)-, ethyl ester | ethyl 2-(methyldithio)propionate | 1.1378 |

TABLE 2-continued

Density Balancing Agents Useful For Balancing Encapsulates Having Cores With a Density of Less Than 1

| Item | CAS Number | Registry Name | Trade name | Specific Gravity 25° C. (g/cm$^3$) |
|---|---|---|---|---|
| 64 | 25485-88-5 | benzoic acid, 2-hydroxy-, cyclohexyl ester | cyclohexyl salicylate | solid |
| 65 | 25628-84-6 | benzoic acid, 2-[(1-oxopropyl)amino]-, methyl ester | anthranilic acid, n-propionyl-, methyl ester | solid |
| 66 | 26486-14-6 | ethanethioic acid, s-(4,5-dihydro-2-methyl-3-furanyl) ester | 2-methyl-3-thioacetoxy-4,5-dihydrofuran | solid |
| 67 | 2719-08-6 | benzoic acid, 2-(acetylamino)-, methyl ester | n-acetyl methyl anthranilate | solid |
| 68 | 2765-04-0 | 1,3,5-trithiane, 2,4,6-trimethyl- | 2,4,6-trimethyl-1,3,5-trithiane | solid |
| 69 | 30954-98-4 | benzoic acid, 2-amino-, propyl ester | propyl anthranilate | solid |
| 70 | 3121-70-8 | butanoic acid, 1-naphthalenyl ester | alpha-naphthyl butyrate | solid |
| 71 | 33662-58-7 | benzoic acid, 2,4-dihydroxy-3-methyl-, methyl ester | methyl 3-methylresorcylate | solid |
| 72 | 34135-85-8 | trisulfide, methyl 2-propenyl | allyl methyl trisulfide | 1.1884 |
| 73 | 34171-46-5 | 2-furanmethanol, benzoate | furfuryl benzoate | solid |
| 74 | 34265-58-2 | benzoic acid, 2-hydroxy-5-methyl-, ethyl ester | ethyl-5-methylsalicylate | solid |
| 75 | 3591-42-2 | benzene, (2,2-dichloro-1-methylcyclopropyl)- | 1,1-dichloro-2-methyl-2-phenylcyclopropane | solid |
| 76 | 36880-33-8 | 2-thiophenecarboxaldehyde, 5-ethyl- | 5-ethyl-2-thiophenecarbaldehyde | solid |
| 77 | 37837-44-8 | benzoic acid, [(phenylmethylene)amino]-, methyl ester | methyl n-benzylidene-2-aminobenzoate | solid |
| 78 | 38325-25-6 | spiro[1,3-dithiolo[4,5-b]furan-2,3'(2'h)-furan], hexahydro-2',3a-dimethyl- | spiro(2,4-dithia-1-methyl-8-oxabicyclo[3.3.0]octane-3,3') | solid |
| 79 | 40527-42-2 | 1,3-benzodioxole, 5-(diethoxymethyl)- | heliotropine diethyl acetal | solid |
| 80 | 40785-62-4 | cyclododeca[c]furan, 1,3,3a,4,5,6,7,8,9,10,11,13a-dodecahydro- | 14-oxabicyclo[10.3.0]-2-pentadecene | solid |
| 81 | 4112-89-4 | benzeneacetic acid, 2-methoxyphenyl ester | guaiacyl phenylacetate | solid |
| 82 | 4265-16-1 | 2-benzofurancarboxaldehyde | 2-benzofurancarboxaldehyde | solid |
| 83 | 43040-01-3 | 1,2,4-trithiane, 3-methyl- | 3-methyl-1,2,4-trithiane | solid |
| 84 | 4437-20-1 | furan, 2,2'-[dithiobis(methylene)]bis- | 2,2'-(dithiomethylene)difuran | 1.3144 |
| 85 | 458-37-7 | 1,6-heptadiene-3,5-dione, 1,7-bis(4-hydroxy-3-methoxyphenyl)-, (e,e)- | curcumin | solid |
| 86 | 4707-47-5 | benzoic acid, 2,4-dihydroxy-3,6-dimethyl-, methyl ester | methyl 2,4-dihydroxy-3,6-dimethylbenzoate | solid |
| 87 | 5446-02-6 | benzoic acid, 2-hydroxy-4-methoxy-, methyl ester | methyl 4-methoxysalicylate | solid |
| 88 | 5461-08-5 | propanoic acid, 2-methyl-, 1,3-benzodioxol-5-ylmethyl ester | piperonyl isobutyrate | solid |
| 89 | 54644-28-9 | 1,2,4-trithiolane, 3,5-diethyl- | 3,5-diethyl-1,2,4-trithiolane | solid |
| 90 | 54934-99-5 | 1,2,4-trithiolane, 3,5-bis(1-methylethyl)- | 3,5-diisopropyl-1,2,4-trithiolane | solid |
| 91 | 57500-00-2 | furan, 2-[(methyldithio)methyl]- | methyl furfuryl disulfide | 1.2240 |
| 92 | 5756-24-1 | tetrasulfide, dimethyl | dimethyl tetrasulfide | 1.4180 |
| 93 | 57568-60-2 | benzeneacetaldehyde, .alpha.-(2-furanylmethylene)- | 2-phenyl-3-(2-furyl)prop-2-enal | solid |
| 94 | 586-38-9 | benzoic acid, 3-methoxy- | 3-methoxybenzoic acid | solid |
| 95 | 5925-68-8 | benzenecarbothioic acid, s-methyl ester | s-ethyl benzothioate | 1.1179 |
| 96 | 606-45-1 | benzoic acid, 2-methoxy-, methyl ester | methyl o-methoxybenzoate | 1.1331 |
| 97 | 607-88-5 | benzoic acid, 2-hydroxy-, 4-methylphenyl ester | p-cresyl salicylate | solid |
| 98 | 607-90-9 | benzoic acid, 2-hydroxy-, propyl ester | propyl salicylate | solid |
| 99 | 6099-03-2 | 2-propenoic acid, 3-(2-methoxyphenyl)- | 2-methoxycinnamic acid | solid |

TABLE 2-continued

Density Balancing Agents Useful For Balancing Encapsulates Having Cores With a Density of Less Than 1

| Item | CAS Number | Registry Name | Trade name | Specific Gravity 25° C. (g/cm³) |
|---|---|---|---|---|
| 100 | 6099-04-3 | 2-propenoic acid, 3-(3-methoxyphenyl)- | 3-methoxycinnamic acid | solid |
| 101 | 6110-36-7 | benzoic acid, 2-hydroxy-4-methoxy-6-methyl-, ethyl ester | 2-hydroxy-4-methoxy-6-methylbenzoic acid, ethyl ester | solid |
| 102 | 613-84-3 | benzaldehyde, 2-hydroxy-5-methyl- | 5-methyl salicylic aldehyde | solid |
| 103 | 614-33-5 | 1,2,3-propanetriol, tribenzoate | glyceryl tribenzoate | solid |
| 104 | 614-34-6 | benzoic acid, 4-methylphenyl ester | p-cresyl benzoate | solid |
| 105 | 615-10-1 | 2-furancarboxylic acid, propyl ester | propyl 2-furoate | 1.1128 |
| 106 | 617-01-6 | benzoic acid, 2-hydroxy-, 2-methylphenyl ester | o-tolyl salicylate | solid |
| 107 | 617-05-0 | benzoic acid, 4-hydroxy-3-methoxy-, ethyl ester | ethyl vanillate | solid |
| 108 | 621-82-9 | 2-propenoic acid, 3-phenyl- | cinnamic acid | solid |
| 109 | 62265-99-0 | benzene, 1,3-dibromo-2-methoxy-4-methyl-5-nitro- | 1,3-dibromo-2-methoxy-4-methyl-5-nitrobenzene | solid |
| 110 | 622-78-6 | benzene, (isothiocyanatomethyl)- | benzyl isothiocyanate | 1.2200 |
| 111 | 623-20-1 | 2-propenoic acid, 3-(2-furanyl)-, ethyl ester | ethyl 3-(2-furyl)-acrylate | 1.1304 |
| 112 | 6258-60-2 | benzenemethanethiol, 4-methoxy- | p-methoxy benzyl mercaptan | 1.1108 |
| 113 | 6258-63-5 | 2-thiophenemethanethiol | thenyl mercaptan | 1.1871 |
| 114 | 65416-19-5 | benzene, 1,1'-[(2-phenylethylidene)bis(oxymethylene)]bis- | phenylacetaldehyde dibenzyl acetal | solid |
| 117 | 67801-43-8 | benzenepropanoic acid, .beta.-oxo-, 4-methylphenyl ester | p-tolyl 3-oxo-3-phenylpropionate | solid |
| 118 | 67860-00-8 | 1h-indole-3-heptanol, .eta.-1h-indol-3-yl-.alpha.,.alpha.,.epsilon.-trimethyl- | indolene | solid |
| 119 | 68555-58-8 | benzoic acid, 2-hydroxy-, 3-methyl-2-butenyl ester | prenyl salicylate | solid |
| 120 | 68844-96-2 | 1,3-benzodioxole-5-propanol, .alpha.-methyl-, acetate | alpha-methyl-1,3-benzodioxole-5-propanol, acetate | solid |
| 121 | 6911-51-9 | thiophene, 2,2'-dithiobis- | 2-thienyl disulfide | solid |
| 122 | 69-72-7 | benzoic acid, 2-hydroxy- | salicylic acid | solid |
| 123 | 698-27-1 | benzaldehyde, 2-hydroxy-4-methyl- | 2-hydroxy-4-methylbenzaldehyde | solid |
| 124 | 699-10-5 | disulfide, methyl phenylmethyl | methyl benzyl disulfide | 1.1382 |
| 125 | 7149-32-8 | 2-furancarboxylic acid, 2-phenylethyl ester | phenethyl 2-furoate | 1.1891 |
| 126 | 7217-59-6 | benzenethiol, 2-methoxy- | 2-methoxy-thiophenol | 1.1530 |
| 127 | 72927-84-5 | benzoic acid, 2-[[(4-hydroxy-3-methoxyphenyl)methylene]amino]-, methyl ester | benzoic acid, 2-[[(4-hydroxy-3-methoxyphenyl)methylene]amino]-, methyl ester | solid |
| 128 | 72987-59-8 | ethanol, 2-(4-methylphenoxy)-1-(2-phenylethoxy)- | algix synarome | 1.1309 |
| 129 | 7492-65-1 | benzeneacetic acid, 3-phenyl-2-propenyl ester | cinnamyl phenylacetate | solid |
| 130 | 7493-63-2 | benzoic acid, 2-amino-, 2-propenyl ester | allyl anthranilate | solid |
| 131 | 75147-23-8 | bicyclo[3.2.1]octan-8-one, 1,5-dimethyl-, oxime | 1,5-dimethyl-bicyclo[3.2.1]octan-8-one, oxime- | solid |
| 132 | 7774-74-5 | 2-thiophenethiol | 2-thienyl mercaptan | 1.2297 |
| 133 | 7774-96-1 | phenol, 2-methoxy-4-(1-propenyl)-, formate | isoeugenyl formate | solid |
| 134 | 7779-16-0 | benzoic acid, 2-amino-, cyclohexyl ester | cyclohexyl anthranilate | solid |
| 136 | 79915-74-5 | benzoic acid, 2-hydroxy-, 2-(1-methylethoxy)ethyl ester | 2-isopropoxyethyl salicylate | solid |
| 137 | 81-14-1 | ethanone, 1-[4-(1,1-dimethylethyl)-2,6-dimethyl-3,5-dinitrophenyl]- | musk ketone | solid |
| 139 | 830-09-1 | 2-propenoic acid, 3-(4-methoxyphenyl)- | 4-methoxycinnamic acid | solid |
| 140 | 83-66-9 | benzene, 1-(1,1-dimethylethyl)-2-methoxy-4-methyl-3,5-dinitro- | musk ambrette | solid |
| 141 | 84-66-2 | 1,2-benzenedicarboxylic acid, diethyl ester | diethyl phthalate | 1.1221 |
| 142 | 85213-22-5 | ethanone, 1-(3,4-dihydro-2h-pyrrol-5-yl)- | 2-acetyl-1-pyrroline | 1.2592 |

TABLE 2-continued

Density Balancing Agents Useful For Balancing Encapsulates Having Cores With a Density of Less Than 1

| Item | CAS Number | Registry Name | Trade name | Specific Gravity 25° C. (g/cm³) |
|---|---|---|---|---|
| 143 | 85-91-6 | benzoic acid, 2-(methylamino)-, methyl ester | dimethyl anthranilate | solid |
| 144 | 87-05-8 | 2h-1-benzopyran-2-one, 7-ethoxy-4-methyl- | 4-methyl-7-ethoxycoumarin | solid |
| 145 | 87-22-9 | benzoic acid, 2-hydroxy-, 2-phenylethyl ester | phenethyl salicylate | solid |
| 146 | 87-25-2 | benzoic acid, 2-amino-, ethyl ester | ethyl anthranilate | 1.1408 |
| 147 | 87-29-6 | 2-propen-1-ol, 3-phenyl-, 2-aminobenzoate | cinnamyl anthranilate | solid |
| 149 | 882-33-7 | disulfide, diphenyl | phenyl disulfide | solid |
| 153 | 91-60-1 | 2-naphthalenethiol | 2-naphthyl mercaptan | solid |
| 154 | 93-08-3 | ethanone, 1-(2-naphthalenyl)- | methyl beta-naphthyl ketone | solid |
| 155 | 93-29-8 | phenol, 2-methoxy-4-(1-propenyl)-, acetate | isoeugenyl acetate | solid |
| 156 | 93-44-7 | 2-naphthalenol, benzoate | 2-naphthyl benzoate | solid |
| 157 | 93-99-2 | benzoic acid, phenyl ester | phenyl benzoate | solid |
| 159 | 94-13-3 | benzoic acid, 4-hydroxy-, propyl ester | propylparaben | solid |
| 160 | 941-98-0 | ethanone, 1-(1-naphthalenyl)- | methyl 1-naphthyl ketone | solid |
| 161 | 94278-27-0 | propanoic acid, 3-[(2-furanylmethyl)thio]-, ethyl ester | ethyl 3-(furfurylthio)propionate | solid |
| 162 | 94-41-7 | 2-propen-1-one, 1,3-diphenyl- | chalcone | solid |
| 163 | 94-44-0 | 3-pyridinecarboxylic acid, phenylmethyl ester | benzyl nicotinate | solid |
| 164 | 94-47-3 | benzoic acid, 2-phenylethyl ester | phenethyl benzoate | solid |
| 165 | 94-62-2 | piperidine, 1-[5-(1,3-benzodioxol-5-yl)-1-oxo-2,4-pentadienyl]-,(e,e)- | piperine | solid |
| 166 | 95-16-9 | benzothiazole | benzosulfonazole | 1.1500 | b) ClogP balancing agents: without being bound by theory, ClogP balancing agents are materials able to increase the total ClogP of said perfume composition in order to facilitate the emulsification of said perfume composition. Suitable ClogP balancing agents are listed in the following table:

|  | CAS | Common name | IUPAC name | ClogP |
|---|---|---|---|---|
| 1 | 6753-98-6 | Amyl_cinnamic_aldehyde,_dilinallyl_acetal | 1,4,8-Cycloundecatriene, 2,6,6,9-tetramethyl-, (E,E,E)- | 6.87 |
| 2 | 84-74-2 | Linolenic_acid | 1,2-Benzenedicarboxylic acid, dibutyl ester | 6.56 |
| 3 | 128-37-0 | Butyl_myristate | Phenol, 2,6-bis(1,1-dimethylethyl)-4-methyl- | 6.51 |
| 4 | 68480-17-1 | Ethyl_heptadecanoate | 3-Pentanone, 1-(2,6,6-trimethyl-2-cyclohexen-1-yl)- | 6.51 |
| 5 | 103-29-7 | Hexyl_dodecanoate | Benzene, 1,1'-(1,2-ethanediyl)bis- | 6.50 |
| 6 | 67801-47-2 | Hexyl_tetradecanoate | Benzoic acid, 2-[(3,7-dimethyl-2,6-octadienylidene)amino]-, methyl | 6.50 |
| 7 | 128-37-0 | Butyl_hexadecanoate | Phenol, 2,6-bis(1,1-dimethylethyl)-4-methyl- | 6.50 |
| 8 | 629-94-7 | Decanoic_acid,_decyl_ester | Heneicosane | 6.50 |
| 9 | 112-41-4 | Isopropyl_palmitate | 1-Dodecene | 6.47 |
| 10 | 10402-47-8 | 2-Methylpropyl_tetradecanoate | Pentanoic acid, 3,7-dimethyl-2,6-octadienyl ester, (E)- | 6.46 |
| 11 | 128-37-0 | Ethyl_pentadecanoate | Phenol, 2,6-bis(1,1-dimethylethyl)-4-methyl- | 6.46 |
| 12 | 117-98-6 | 3-Methylbutyl_tetradecanoate | 6-Azulenol, 1,2,3,3a,4,5,6,8a-octahydro-4,8-dimethyl-2-(1-methylethylidene)-, acetate | 6.45 |
| 13 | 122-62-3 | Ethyl_stearate | Decanedioic acid, bis(2-ethylhexyl) ester | 6.45 |
| 14 | 20407-84-5 | Isopropyl_myristate | 2-Dodecenal, (E)- | 6.44 |
| 15 | 5132-75-2 | Hexadecyl_acetate | Heptanoic acid, octyl ester | 6.44 |

-continued

|   | CAS | Common name | IUPAC name | ClogP |
|---|-----|-------------|------------|-------|
| 16 | 67801-47-2 | 2-Methylpropyl_hexadecanoate | Benzoic acid, 2-[(3,7-dimethyl-2,6-octadienylidene)amino]-, methyl | 6.43 |
| 17 | 112-40-3 | Methyl_hexadecanoate | Dodecane | 6.41 |
| 18 | 3915-83-1 | Ethyl_oleate | Butanoic acid, 3-methyl-, 3,7-dimethyl-2,6-octadienyl ester, (Z)- | 6.41 |
| 19 | 10024-64-3 | Methyl_stearate | Octanoic acid, 1-ethenyl-1,5-dimethyl-4-hexenyl ester | 6.41 |
| 20 | 6624-58-4 | Decyl_phthalate | Hexanoic acid, 1-methylhexyl ester | 6.40 |
| 21 | 112-37-8 | 9-Heptadecanone | Undecanoic acid | 6.40 |
| 22 | 1166-52-5 | Methyl_oleate | Benzoic acid, 3,4,5-trihydroxy-, dodecyl ester | 6.35 |
| 23 | 128-37-0 | alpha-Camphorene | Phenol, 2,6-bis(1,1-dimethylethyl)-4-methyl- | 6.34 |
| 24 | 128-37-0 | Butyl_oleate | Phenol, 2,6-bis(1,1-dimethylethyl)-4-methyl- | 6.31 |
| 25 | 65405-77-8 | Ethyl_linoleate | Benzoic acid, 2-hydroxy-, 3-hexenyl ester, (Z)- | 6.31 |
| 26 | 3915-83-1 | Ethyl_myristate | Butanoic acid, 3-methyl-, 3,7-dimethyl-2,6-octadienyl ester, (Z)- | 6.30 |
| 27 | 6624-58-4 | Dodecyl_isobutyrate | Hexanoic acid, 1-methylhexyl ester | 6.30 |
| 28 | 20407-84-5 | Butyl_stearate | 2-Dodecenal, (E)- | 6.29 |
| 29 | 128-37-0 | Didodecyl_phthalate | Phenol, 2,6-bis(1,1-dimethylethyl)-4-methyl- | 6.28 |
| 30 | 112-37-8 | Dodecyl_butyrate | Undecanoic acid | 6.27 |
| 31 | 1731-88-0 | Methyltetradecylketone | Tridecanoic acid, methyl ester | 6.27 |
| 32 | 68039-38-3 | Adimoll_DO | 2-Butenoic acid, 3,7-dimethyl-6-octenyl ester | 6.25 |
| 33 | 5132-75-2 | 2-Methylpropyl_dodecanoate | Heptanoic acid, octyl ester | 6.24 |
| 34 | 644-08-6 | 4-Methylphenyl_dodecanoate | 1,1'-Biphenyl, 4-methyl- | 6.19 |
| 35 | 2153-28-8 | alpha-bisabolene | Butanoic acid, 1-methyl-1-(4-methyl-3-cyclohexen-1-yl)ethyl ester | 6.19 |
| 36 | 110-38-3 | Ethylhexyl_palmitate | Decanoic acid, ethyl ester | 6.18 |
| 37 | 101-86-0 | Stearic_acid,_isopentyl_ester | Octanal, 2-(phenylmethylene)- | 6.17 |
| 38 | 111-01-3 | Squalene | Tetracosane, 2,6,10,15,19,23-hexamethyl- | 6.17 |
| 39 | 5132-75-2 | Benzyl_laurate | Heptanoic acid, octyl ester | 6.13 |
| 40 | 112-37-8 | 2-Pentadecanone | 2-Pentadecanone | 6.10 |
| 41 | 24717-85-9 | Methyl_linoleate | 2-Butenoic acid, 2-methyl-, 3,7-dimethyl-6-octenyl ester, (E)- | 6.09 |
| 42 | 68039-38-3 | iso_Propyl_dodecanoate | 2-Butenoic acid, 3,7-dimethyl-6-octenyl ester | 6.05 |
| 43 | 1166-52-5 | Methyl_myristate | Benzoic acid, 3,4,5-trihydroxy-, dodecyl ester | 6.02 |
| 44 | 112-63-0 | Palmitoleic_acid | 9,12-Octadecadienoic acid (Z,Z)-, methyl ester | 6.01 |
| 45 | 141-16-2 | Phytyl_acetate | Butanoic acid, 3,7-dimethyl-6-octenyl ester | 6.01 |
| 46 | 128-37-0 | Propyl_laurate | Phenol, 2,6-bis(1,1-dimethylethyl)-4-methyl- | 6.01 |
| 47 | 10402-47-8 | Linalyl_octanoate | Pentanoic acid, 3,7-dimethyl-2,6-octadienyl ester, (E)- | 6.00 |
| 48 | 79-78-7 | Nerolidyl_isobutyrate | 1,6-Heptadien-3-one, 1-(2,6,6-trimethyl-2-cyclohexen-1-yl)- | 5.98 |
| 49 | 68039-38-3 | 6,10,14-trimethyl-2-Pentadecanone | 2-Butenoic acid, 3,7-dimethyl-6-octenyl ester | 5.98 |
| 50 | 84012-64-6 | 2-Pentadecanone,_6,10,14-trimethyl- | 1-Cyclopentene-1-propanol, .beta.,.beta.,2-trimethyl-5-(1- | 5.98 |
| 51 | 112-54-9 | Ethyl_linolenate | Dodecanal | 5.97 |
| 52 | 24717-85-9 | 1-Dodecene | 2-Butenoic acid, 2-methyl-, 3,7-dimethyl-6-octenyl ester, (E)- | 5.95 |
| 53 | 3915-83-1 | alpha-Farnesene | Butanoic acid, 3-methyl-, 3,7-dimethyl-2,6-octadienyl ester, (Z)- | 5.95 |

-continued

| | CAS | Common name | IUPAC name | ClogP |
|---|---|---|---|---|
| 54 | 6281-40-9 | n-Pentyl_decanoate | Hexanoic acid, 3-phenylpropyl ester | 5.95 |
| 55 | 128-37-0 | Heptyl_octanoate | Phenol, 2,6-bis(1,1-dimethylethyl)-4-methyl- | 5.94 |
| 56 | 68459-99-4 | Oleic_acid | 1-Penten-3-one, 4-methyl-1-(2,6,6-trimethyl-2-cyclohexen-1-yl)- | 5.94 |
| 57 | 137085-37-1 | Octyl_heptanoate | 1-Penten-3-ol, 1-(2,6,6-trimethyl-1-cyclohexen-1-yl)-, acetate | 5.94 |
| 58 | 7493-82-5 | Myristaldehyde | Heptanoic acid, pentyl ester | 5.86 |
| 59 | 67801-47-2 | Cyclohexyl_amyl_sulfide_in_diethyl_phthalate | Benzoic acid, 2-[(3,7-dimethyl-2,6-octadienylidene)amino]-, methyl | 5.77 |
| 60 | 67874-72-0 | Hendecane | Cyclohexanol, 2-(1,1-dimethylpropyl)-, acetate | 5.73 |
| 61 | 150-60-7 | (+)-Cuparene | Disulfide, bis(phenylmethyl) | 5.73 |
| 62 | 101-86-0 | Lauryl_acetate | Octanal, 2-(phenylmethylene)- | 5.73 |
| 63 | 3915-83-1 | Dodecane | Butanoic acid, 3-methyl-, 3,7-dimethyl-2,6-octadienyl ester, (Z)- | 5.72 |
| 64 | 3915-83-1 | Hexadecanenitrile_(9CI) | Butanoic acid, 3-methyl-, 3,7-dimethyl-2,6-octadienyl ester, (Z)- | 5.72 |
| 65 | 106-29-6 | Benzoic_acid,_3,4,5-trihydroxy-,_dodecyl_ester_(9CI) | Butanoic acid, 3,7-dimethyl-2,6-octadienyl ester, (E)- | 5.68 |
| 66 | 67801-47-2 | 2-Methylpropyl_decanoate | Benzoic acid, 2-[(3,7-dimethyl-2,6-octadienylidene)amino]-, methyl | 5.68 |
| 67 | 67801-47-2 | Butyl_decanoate | Benzoic acid, 2-[(3,7-dimethyl-2,6-octadienylidene)amino]-, methyl | 5.67 |
| 68 | 638-25-5 | Methyl_linolenate | Octanoic acid, pentyl ester | 5.64 |
| 69 | 3915-83-1 | beta-Guaiene | Butanoic acid, 3-methyl-, 3,7-dimethyl-2,6-octadienyl ester, (Z)- | 5.63 |
| 70 | 67801-47-2 | Dipentyl_sulphide | Benzoic acid, 2-[(3,7-dimethyl-2,6-octadienylidene)amino]-, methyl | 5.62 |
| 71 | 51532-26-4 | Hexyl_octanoate | Octanoic acid, 3,7-dimethyl-2,6-octadienyl ester, (E)- | 5.62 |
| 72 | 59056-62-1 | Farnesyl_methyl_ether | 2,3b-Methano-3bH-cyclopenta[1,3]cyclopropa[1,2]benzene-4-methanol, octahydro-7,7,8,8-tetramethyl-, acetate | 5.60 |
| 73 | 463-40-1 | 1,1,6-Trimethyltetraline | 9,12,15-Octadecatrienoic acid, (Z,Z,Z)- | 5.58 |
| 74 | 7774-82-5 | alpha-Santalene | 2-Tridecenal | 5.56 |
| 75 | 493-01-6 | Verdantiol | Naphthalene, decahydro-, cis- | 5.56 |
| 76 | 128-37-0 | Helvetolide | Phenol, 2,6-bis(1,1-dimethylethyl)-4-methyl- | 5.56 |
| 77 | 67801-47-2 | Dicyclohexyl_disulfide | Benzoic acid, 2-[(3,7-dimethyl-2,6-octadienylidene)amino]-, methyl | 5.55 |
| 78 | 128-37-0 | (E,E)-6,10,14-trimethyl-5,9,13-Pentadecatrien-2-one | Phenol, 2,6-bis(1,1-dimethylethyl)-4-methyl- | 5.54 |
| 79 | 67801-47-2 | Citronellyl_caproate | Benzoic acid, 2-[(3,7-dimethyl-2,6-octadienylidene)amino]-, methyl | 5.52 |
| 80 | 67801-47-2 | 2,6,10-Trimethylundecanal | Benzoic acid, 2-[(3,7-dimethyl-2,6-octadienylidene)amino]-, methyl | 5.49 |
| 81 | 128-37-0 | Cadinene | Phenol, 2,6-bis(1,1-dimethylethyl)-4-methyl- | 5.47 |
| 82 | 32214-91-8 | Celestolide | Bicyclo[7.2.0]undec-3-en-5-ol, 4,11,11-trimethyl-8-methylene-, acetate | 5.47 |
| 83 | 128-37-0 | Linalyl_phenylacetate | Phenol, 2,6-bis(1,1-dimethylethyl)-4-methyl- | 5.46 |
| 84 | 638-25-5 | Tridecanal | Octanoic acid, pentyl ester | 5.44 |
| 85 | 67801-47-2 | 2-Octylthiophene | Benzoic acid, 2-[(3,7-dimethyl-2,6-octadienylidene)amino]-, methyl | 5.44 |
| 86 | 128-37-0 | 3-Tridecanone | Phenol, 2,6-bis(1,1-dimethylethyl)-4-methyl- | 5.44 |
| 87 | 67801-47-2 | Galaxolide | Benzoic acid, 2-[(3,7-dimethyl-2,6-octadienylidene)amino]-, methyl | 5.43 |
| 88 | 128-37-0 | 3-Methyldodecanenitrile | Phenol, 2,6-bis(1,1-dimethylethyl)-4-methyl- | 5.39 |
| 89 | 1731-86-8 | Undecanal_diethyl_acetal | Undecanoic acid, methyl ester | 5.38 |
| 90 | 6876-13-7 | 2,2,4,6,6-Pentamethylheptane | Bicyclo[3.1.1]heptane, 2,6,6-trimethyl-, (1.alpha.,2.beta.,5.alpha.)- | 5.35 |

|  | CAS | Common name | IUPAC name | ClogP |
|---|---|---|---|---|
| 91 | 79-78-7 | beta-Patchoulline | 1,6-Heptadien-3-one, 1-(2,6,6-trimethyl-2-cyclohexen-1-yl)- | 5.34 |
| 93 | 79-78-7 | Octyl_phenylacetate | 1,6-Heptadien-3-one, 1-(2,6,6-trimethyl-2-cyclohexen-1-yl)- | 5.32 |
| 94 | 117-98-6 | Undecyl_acetate | 6-Azulenol, 1,2,3,3a,4,5,6,8a-octahydro-4,8-dimethyl-2-(1-methylethylidene)-, acetate | 5.30 |
| 95 | 638-25-5 | Octyl_2-methylbutyrate | Octanoic acid, pentyl ester | 5.29 |
| 96 | 67801-47-2 | delta-Tetradecalactone | Benzoic acid, 2-[(3,7-dimethyl-2,6-octadienylidene)amino]-, methyl | 5.29 |
| 97 | 37165-63-2 | Octyl_isovalerate | Nonanoic acid, 2-hexyl- | 5.29 |
| 98 | 68039-38-3 | Isobutyl_nonanoate | 2-Butenoic acid, 3,7-dimethyl-6-octenyl ester | 5.28 |
| 100 | 39900-38-4 | Rhodinyl_butyrate | 1H-3a,7-Methanoazulen-6-ol, octahydro-3,6,8,8-tetramethyl-, formate, [3R-(3.alpha.,3a.beta.,6.alpha.,7.beta.,8a.alpha.)]- | 5.26 |
| 101 | 23726-92-3 | Cyclohexanone,_2,4-bis(1,1-dimethylethyl)- | 2-Buten-1-one, 1-(2,6,6-trimethyl-1-cyclohexen-1-yl)-, (Z)- | 5.26 |
| 102 | 67801-47-2 | Dihexyl_fumarate | Benzoic acid, 2-[(3,7-dimethyl-2,6-octadienylidene)amino]-, methyl | 5.26 |
| 103 | 128-37-0 | Isopropyl_10-undecenoate | Phenol, 2,6-bis(1,1-dimethylethyl)-4-methyl- | 5.25 | c) Vapor pressure balancing agents: the vapor pressure provides a gauge of the rate of evaporation and the odor strength of the perfume composition. While not being bound by theory, when the vapor pressure of the encapsulate's core is balanced, the encapsulate provides a longer lasting and more consistent core material release.

We can use materials having a low vapor pressure to improve the longevity of the release (see table below).

| CAS Number | Common name | IUPAC Name | Vapor Pressure Log of mm of Hg | Boiling point (° C.) |
|---|---|---|---|---|
| 40785-62-4 | 14-Oxabicyclo[10.3.0]-2-pentadecene | Cyclododeca[c]furan, 1,3,3a,4,5,6,7,8,9,10,11,13a-dodecahydro- | −12.50 | 149.3 |
| 67785-71-1 | Amyl cinnamic aldehyde, dilinallyl acetal | Benzene, [2-[bis[(1-ethenyl-1,5-dimethyl-4-hexenyl)oxy]methyl]-1- | −12.19 | 374.8 |
| 67785-74-4 | Undecylenic aldehyde digeranyl acetal | 1-Undecene, 11,11-bis[(3,7-dimethyl-2,6-octadienyl)oxy]- | −10.92 | 158.4 |
| 111-02-4 | Squalene | 2,6,10,14,18,22-Tetracosahexaene, 2,6,10,15,19,23-hexamethyl-, (all-E)- | −10.51 | 247.0 |
| 111-01-3 | Squalane | Tetracosane, 2,6,10,15,19,23-hexamethyl- | −8.93 | 417.3 |
| 142-77-8 | Butyl oleate | 9-Octadecenoic acid (Z)-, butyl ester | −6.54 | 358.4 |
| 1191-41-9 | Ethyl linolenate | 9,12,15-Octadecatrienoic acid, ethyl ester, (Z,Z,Z)- | −6.37 | 294.5 |
| 544-35-4 | Ethyl linoleate | 9,12-Octadecadienoic acid (Z,Z)-, ethyl ester | −5.90 | 305.1 |
| 111-62-6 | Ethyl oleate | 9-Octadecenoic acid (Z)-, ethyl ester | −5.70 | 337.0 |
| 140-25-0 | Benzyl laurate | Dodecanoic acid, phenylmethyl ester | −5.35 | 296.3 |
| 122-69-0 | Cinnamyl cinnamate | 2-Propenoic acid, 3-phenyl-, 3-phenyl-2-propenyl ester | −5.23 | 351.2 |
| 10402-33-2 | Eugenyl phenylacetate | Benzeneacetic acid, 2-methoxy-4-(2-propenyl)phenyl ester | −5.22 | 372.9 |
| 102-22-7 | Geranyl phenylacetate | Benzeneacetic acid, 3,7-dimethyl-2,6-octadienyl ester, (E)- | −5.10 | 272.9 |
| 7143-69-3 | Linalyl phenylacetate | Benzeneacetic acid, 1-ethenyl-1,5-dimethyl-4-hexenyl ester | −5.04 | 329.3 |
| 139-70-8 | Citronellyl phenylacetate | Benzeneacetic acid, 3,7-dimethyl-6-octenyl ester | −4.83 | 283.3 |
| 142-91-6 | Isopropyl palmitate | Hexadecanoic acid, 1-methylethyl ester | −4.45 | 331.3 |
| 544-63-8 | Myristic acid | Tetradecanoic acid | −3.86 | 330.4 |
| 67634-02-0 | Phenylacetaldehyde digeranyl acetal | Benzene, [2,2-bis[(3,7-dimethyl-2,6-octadienyl)oxy]ethyl]- | −3.31 | 284.3 |
| 629-97-0 | n-Docosane | Docosane | −3.23 | 318.8 |
| 67785-69-7 | Amyl cinnamic aldehyde, digeranyl acetal | Benzene, [2-[bis[(3,7-dimethyl-2,6-octadienyl)oxy]methyl]-1- | −3.08 | 296.8 |
| 65416-19-5 | Phenylacetaldehyde dibenzyl acetal | Benzene, 1,1'-[(2-phenylethylidene)bis(oxymethylene)]bis- | −2.25 | 266.5 |
| 57-11-4 | Stearic acid | Octadecanoic acid | −1.73 | 246.2 |

-continued

| CAS Number | Common name | IUPAC Name | Vapor Pressure Log of mm of Hg | Boiling point (° C.) |
|---|---|---|---|---|
| 7493-80-3 | alpha-Amylcinnamyl isovalerate | Butanoic acid, 3-methyl-, 2-(phenylmethylene)heptyl ester | −1.68 | 248.4 | or we can even use materials with a high vapor pressure for a fast release (see table below).

| CAS Number | Common name | IUPAC Name | Vapor Pressure Log of mm of Hg | Boiling point (° C.) |
|---|---|---|---|---|
| 6175-49-1 | Decyl methyl ketone | 2-Dodecanone | 0.67 | 160.8 |
| 112-44-7 | Undecanal | Undecanal | −1.49 | 236.8 |
| 7289-52-3 | Decyl methyl ether | Decane, 1-methoxy- | −1.19 | 217.5 |
| 112-40-3 | Dodecane | Dodecane | −0.75 | 195.2 |
| 22810-10-2 | Citronellyl ethyl ether | Octane, -ethoxy-3,7-dimethyl- | −1.03 | 207.8 |
| 112-41-4 | 1-Dodecene | 1-Dodecene | −1.00 | 196.7 |
| 1120-21-4 | Hendecane | Undecane | −0.25 | 177.5 |
| 124-18-5 | n-Decane | n-Decane | 0.24 | 159.6 |
| 2436-90-0 | Dihydromyrcene | 1,6-Octadiene, 3,7-dimethyl- | −0.22 | 156.7 |

Process of Making Encapsulates

A process of making a consumer product comprising combining a consumer product adjunct material and a population of encapsulates is disclosed.

In one aspect of said process, said population of encapsulates might be made by:

a) combining a second solution and a second composition to form a third composition and optionally combining any processing aids and said third composition, said second solution comprising based on total weight from about 10% to about 90% water, and water miscible monomer comprises a material selected from the group consisting of a diamine, a triamine and mixtures thereof, in one aspect, said diamines and triamines may be selected from the group consisting of diethylene triamine, hexamethylene diamine, ethylene diamine and mixtures thereof, in one aspect, said second solution is cooled, in one aspect to a temperature of from about 0° C. to about 25° C. said second composition being made by combining, at temperature of from about 0° C. to about 25° C., a first composition and a first solution and emulsifying said combination of said first composition and said first solution,
  (i) said first composition being made by combining based on total first composition weight, from about 65% to about 97% core material, and a water immiscible organic monomer selected from the group consisting of dichlorides, triacyl chlorides and mixtures thereof, in one aspect, said dichlorides may be selected from the group consisting of sebacoyl dichloride, adipoyl dichloride, and mixtures thereof and said triacyl chlorides may be selected from the group consisting of teraphthaloyl chloride, trimesoyl chloride, acetyl chloride, benzoyl chloride, 1,3,5-benzentricarbonyl chloride, and mixtures thereof and cooling said first composition, in one aspect, to a temperature of from about 0° C. to about 25° C., said core material comprising a perfume composition, said perfume composition comprising perfume raw materials having a ClogP of from about 2.0 to about 4.5, or even from about 2.5 to about 4.25, in one aspect, said core material is cooled, in one aspect to a temperature of from about 0° C. to about 25° C.;
  (ii) said first solution comprising, based on total first solution weight, from about 0.1% to about 5%, of an emulsifier, in one aspect, said emulsifier comprises polyvinyl alcohol, in one aspect, said first solution is cooled, in one aspect to a temperature of from about 0° C. to about 25° C., suitable emulsifiers are polysaccharides such as xanthan gum, saccharose derivatives and celluloses, ligninsulfonates, gelatine, starch, fatty acid esters, fatty amines, fatty acid amines, polyglycol esters and polypropylene glycol) esters, poly(vinyl) alcohol, sorbitan monostearate, polysorbate and mixtures thereof. Further suitable emulsifiers can be found in U.S. Pat. No. 6,264,961.

b) stirring said third composition for at least 15 minutes at a temperature of from about 0° C. to about 25° C. and optionally combining any processing aids to said third composition;

c) optionally, preparing a third solution comprising based on total weight from about 10% to about 90% water, and one or more water miscible monomers comprising a different di-amine and/or triamine from the di-amine(s) and/or a triamine(s) used in the second solution. In one aspect such di- and triamines may comprise diethylene triamine, hexamethylene diamine, ethylene diamine, and cooling this third solution, in one aspect, to a temperature of from about 0° C. to about 25° C. Combining said third solution with said third composition to form a fourth composition.

d) optionally, preparing a fourth solution comprising based on total weight from about 10% to about 90% water, and one or more water miscible monomers comprising a different di-amine and/or triamine from the di-amine(s) and/or a triamine(s) used in the second and third solutions. In one aspect said di- and triamines may comprise diethylene triamine, hexamethylene diamine, ethylene diamine, and cooling this third solution, in one aspect, to a temperature of from about 0° C. to about 25° C. Combining said fourth solution with said fourth composition to form a fifth composition.

e) optionally, centrifugating and or decanting the encapsulates from the third, fourth or fifth composition, and cleaning the encapsulates with deionized water.

f) optionally combining a scavenger material, neutralizing agent, structurant, salts and/or anti-agglomeration agent with said third, fourth or fifth composition during step g.) or thereafter;

g) optionally spray drying or agglomerating said third, fourth or fifth composition.

Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.), Ingeniatrics (Sevilla, Spain), ProcepT (Zelzate, Belgium), Vidrafoc (Barcelona, Spain).

Adjunct Materials

While not essential for each consumer product embodiment of the present invention, the non-limiting list of adjuncts illustrated hereinafter are suitable for use in the instant consumer products and may be desirably incorporated in certain embodiments of the invention, for example to assist or enhance performance, for treatment of the substrate to be cleaned, or to modify the aesthetics of the composition as is the case with perfumes, colorants, dyes or the like. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, thickeners/structurants, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential for each consumer product embodiment of the present invention. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, thickeners/structurants, fabric softeners, carriers, hydrotropes, processing aids and/or pigments. However, when one or more adjuncts is present, such one or more adjuncts may be present as detailed below.

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders, polycarboxylate compounds, ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo [6.6.2]hexa-decane.

Suitable transition metal MRLs are readily prepared by known procedures, such as taught for example in WO 00/32601, and U.S. Pat. No. 6,225,464.

Suitable thickeners/structurants and useful levels of same are described in U.S. Patent Application Publication No. 2005/0130864 A1 and U.S. Pat. Nos. 7,169,741 B2 and 7,297,674 B2. In one aspect, the thickener may be a rheology modifier. The rheology modifier may be selected from the group consisting of non-polymeric crystalline, hydroxy-functional materials, polymeric rheology modifiers which impart shear thinning characteristics to the aqueous liquid matrix of the composition. In one aspect, such rheology modifiers impart to the aqueous liquid composition a high shear viscosity, at 20 $sec^{-1}$ shear rate and at 21° C., of from 1 to 7000 cps and a viscosity at low shear (0.5 $sec^{-1}$ shear rate at 21° C.) of greater than 1000 cps, or even 1000 cps to 200,000 cps. In one aspect, for cleaning and treatment compositions, such rheology modifiers impart to the aqueous liquid composition a high shear viscosity, at 20 $sec^{-1}$ and at 21°C., of from 50 to 3000 cps and a viscosity at low shear (0.5 $sec^{-1}$ shear rate at 21° C.) of greater than 1000 cps, or even 1000 cps to 200,000 cps. Viscosity according to the present invention is measured using an AR 2000 rheometer from TA instruments using a plate steel spindle having a plate diameter of 40 mm and a gap size of 500 µm. The high shear viscosity at 20 $sec^{-1}$ and low shear viscosity at 0.5 $sec^{-1}$ can be obtained from a logarithmic shear rate sweep from 0.1 $sec^{-1}$ to 25 $sec^{-1}$ in 3 minutes time at 21° C. Crystalline hydroxyl functional materials are rheology modifiers which form thread-like structuring systems throughout the matrix of the composition upon in situ crystallization in the matrix. Polymeric rheology modifiers are selected from the group consisting of polyacrylates, polymeric gums, other non-gum polysaccharides, and combinations of these polymeric materials.

Generally, the rheology modifier will comprise from about 0.01% to about 1% by weight, from about 0.05% to about 0.75% by weight, or even from about 0.1% to about 0.5% by weight, of the compositions herein.

Structuring agent which are especially useful in the compositions of the present invention comprises non-polymeric (except for conventional alkoxylation), crystalline hydroxy-functional materials which can form thread-like structuring systems throughout the liquid matrix when they are crystallized within the matrix in situ. Such materials can be generally characterized as crystalline, hydroxyl-containing fatty acids, fatty esters or fatty waxes. In one aspect, rheology modifiers include crystalline, hydroxyl-containing rheology modifiers include castor oil and its derivatives. In one aspect, rheology modifiers may include hydrogenated castor oil derivatives such as hydrogenated castor oil and hydrogenated castor wax. Commercially available, castor oil-based, crystalline, hydroxyl-containing rheology modifiers include THIXCIN™ from Rheox, Inc. (now Elementis).

Other types of rheology modifiers, besides the non-polymeric, crystalline, hydroxyl-containing rheology modifiers described heretofore, may be utilized in the liquid detergent compositions herein. Polymeric materials which provide shear-thinning characteristics to the aqueous liquid matrix may also be employed.

Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan (gum Arabic), carrageenan, gellan gum, xanthan gum and guar gum.

If polymeric rheology modifiers are employed herein, a preferred material of this type is gellan gum. Gellan gum is a heteropolysaccharide prepared by fermentation of Pseudomonaselodea ATCC 31461. Gellan gum is commercially marketed by CP Kelco U.S., Inc. under the KELCO-GEL tradename.

A further alternative and suitable rheology modifier include a combination of a solvent and a polycarboxylate polymer. More specifically the solvent may be an alkylene glycol. In one aspect, the solvent may compriser dipropylene glycol. In one aspect, the polycarboxylate polymer may comprise a polyacrylate, polymethacrylate or mixtures thereof. In one aspect, solvent may be present, based on total composition weight, at a level of from 0.5% to 15%, or from 2% to 9% of the composition. In one aspect, polycarboxylate polymer may be present, based on total composition weight, at a level of from 0.1% to 10%, or from 2% to 5%. In one aspect, the solvent component may comprise mixture of dipropylene glycol and 1,2-propanediol. In one aspect, the ratio of dipropylene glycol to 1,2-propanediol may be 3:1 to 1:3, or even 1:1. In one aspect, the polyacrylate may comprise a copolymer of unsaturated mono- or di-carbonic acid and $C_1$-$C_{30}$ alkyl ester of the (meth) acrylic acid. In another aspect, the rheology modifier may comprise a polyacrylate of unsaturated mono- or di-carbonic acid and $C_1$-$C_{30}$ alkyl ester of the (meth) acrylic acid. Such copolymers are available from Noveon Inc under the tradename Carbopol Aqua 30®. In the absence of rheology modifier and in order to impart the desired shear thinning characteristics to the liquid composition, the liquid composition can be internally structured through surfactant phase chemistry or gel phases.

Processes of Making and Using Compositions

The embodiments of the compositions of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Method of Use

Compositions disclosed herein that contain the encapsulate disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with a encapsulate according to the present invention or composition comprising said encapsulate and then optionally washed and/or rinsed. For purposes of the present invention, washing includes but is not limited to, scrubbing, and mechanical agitation. The situs may comprise most any material, for example a fabric, fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Test Methods

It is understood that the test methods that are disclosed in the Test Methods Section of the present application are used to determine the respective values of the parameters of Applicants' invention as such invention is described and claimed herein.

(1) Sample Preparation For Test Methods (if Sample is in a Slurry Form)

Before the encapsulate slurries can be used for the described tests, the sample is homogenized by shaking the sample for 20 minutes on a shaking table such as the Heidolph Promax 2020. Once homogenized, a 200 ml glass jar is filled with the slurry. This glass jar is then put on storage for the required time and condition. After the storage period, each 200 ml sample is again homogenized for 20 minutes on the shaking table. After homogenization the slurry is used for the experiments.

(1) Fracture Strength a.) Place 1 gram of particles in 1 liter of distilled deionized (DI) water.

b.) Permit the particles to remain in the DI water for 10 minutes and then recover the particles by filtration, using a 60 mL syringe filter, 1.2 micron nitrocellulose filter (Millipore, 25 mm diameter).

c.) Determine the rupture force of 30 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the fracture strength of each particle by dividing the rupture force (in Newtons) by the cross-sectional area of the respective spherical particle ($\pi r^2$, where r is the radius of the particle before compression), said cross-sectional area being determined as follows: measuring the particle size of each individual particle using the experimental apparatus and method of Zhang, Z.; Sun, G; "Mechanical Properties of Melamine-Formaldehyde microcapsules," J. Microencapsulation, vol 18, no. 5, pages 593-602, 2001.

d.) Use the 30 independent measurements from c.) above, and calculate the percentage of particles having a fracture strength within the claimed range fracture strength range.

(3) Mean Particle Size

The mean particle size of the wax coated particles is determined using a Lasentec M500L-316-K supplied by Mettler-Toledo, Inc., 1900 Polaris Parkway, Columbus, Ohio, 43240, US. The equipment is setup (Lasentec, FBRM Control Interface, version 6.0) as described in the Lasentec manuel, issued February 2000. Software setup and sample analysis is performed using Windows software (Windows XP, version 2002) in the WINDOWS manual.

(4) Particle Wall Thickness

All references to Leica Microsystems refer to the Company with Corporate Headquarters located at:
Leica Microsystems GmbH
Ernst-Leitz-Strasse 17-37
35578 Wetzlar All references to Drummond refer to the Company located at:
Drummond Scientific Company
500 Parkway, Box 700
Broomall, Pa. 19008

All references to Hitachi refer to the Company with Corporate Headquarters located at:
Hitachi High Technologies
24-14, Nishi-Shimbashi 1-chome, Minato-ku,
Tokyo 105-8717, Japan All references to Gatan refer to the Company with Corporate Headquarters located at:
Gatan, Inc.
5933 Coronado Lane
Pleasanton, Calif. 94588

All references to Quartz refer to the Company with offices located at:
Quartz Imaging Corporation
Technology Enterprise Facility III
6190 Agronomy Rd, Suite 406
Vancouver, B.C. Canada V6T 1Z3

Materials:
Methylcyclohexane—Alfa Aesar Catalogue Number A16057 or equivalent
Capillary Pipettes—Drummond Catalogue Number 5-000-1005 or equivalent
Flat Specimen Carrier—Leica Microsystems P/N 706897 or equivalent
Copper Washers—Leica Microsystems P/N 706867 or equivalent
Flat Specimen Pod—Leica Microsystems P/N 706839 or equivalent
Loading Device for Flat Specimen Holder—Leica Microsystems P/N 706832 or equivalent
Torque Wrench—Leica Microsystems P/N 870071 or equivalent
Allen Bit, 2—Leica Microsystems P/N 870072 or equivalent
Forceps—Leica Microsystems P/N 840105 or equivalent
Gatan Planchette Collet—Gatan P/N PEP5099
Gatan Planchette Specimen Holder—Gatan P/N PEP1395

Instruments:
Scanning Electron Microscope—Hitachi Model S-5200 SEM/STEM or equivalent
High Pressure Freezer—Leica Microsystems Model 706802 EM Pact or equivalent
Cryotransfer Device—Gatan Model CT3500 or equivalent
Cryotransfer System—Gatan Model CT2500 or equivalent
Gatan ITC Temperature Controller—Gatan Model ITC502 or equivalent
Image Analysis Software—Quartz PCI Version 5 or equivalent Sample: Obtain the sample of microcapsules as per the procedure of 1 above entitled "Fracture Strength". 50 samples are required.

Test Procedure
1) Turn on the Leica Microsystems High Pressure Freezer (Leica Microsystems Model Number 706802).

2) Fill up the methylcyclohexane container on the High Pressure Freezer with methylcyclohexane (Alfa Aesar Cat. # A16057 or equivalent).
3) Fill up the liquid nitrogen dewar on the High Pressure Freezer.
4) Fill the liquid nitrogen bath on the High Pressure Freezer
5) The display on the High Pressure Freezer will show Load Sample on the front panel when the instrument is ready to use.
6) Start the Hitachi Model S-5200 SEM/STEM and set the Accelerating Voltage to 3.0 KV and the Emission Current to 20 µA.
7) Fill the Anti-contaminator Dewar located on the lower right side of the Hitachi Model S-5200 SEM/STEM microscope column with liquid nitrogen.
8) Fill the liquid nitrogen dewar on the Gatan Alto 2500 Cryotransfer System (Gatan Model CT2500). Replenish the liquid nitrogen until the dewar remains full. The device is ready to use when the prepchamber temperature reads below −190° C.
9) Place a copper washer (Leica Microsystems P/N 706867) on top of the flat specimen carrier such that the hole in the washer aligns with the well in the flat specimen carrier.
10) Take a glass capillary pipette (Drummond P/N 5-000-1005 or similar) and insert the provided wire plunger into one end of the pipette
11) Insert the pipette into the microcapsule dispersion and withdraw the plunger part way to pull a few microliters of the dispersion into the pipette.
12) Place the tip of the pipette in the well in the flat specimen carrier and push the plunger into the pipette to dispense a small amount of liquid until the well is just slightly overfilled.
13) Insert a 2 mm Allen key bit (Leica Microsystems P/N 870072) into the torque wrench (Leica Microsystems P/N 870071).
14) Using the torque wrench with the bit, loosen the Diamond Locking Screw in the Flat Specimen Pod (Leica Microsystems P/N 706839).
15) Place the Flat Specimen Holder and Copper Washer into the Flat Specimen Pod.
16) Use the torque wrench with the 2 mm Allen key bit to tighten the Diamond Locking
Screw in the Flat Specimen Pod onto the specimen until the torque wrench clicks twice.
17) Attach the Loading Device for the Flat Specimen Holder (Leica Microsystems P/N 706832) to the Flat Specimen Pod by screwing it onto the exposed threads of the Diamond Locking Screw.
18) Place the Loading Device for the Flat Specimen Holder with the Flat Specimen Pod onto the EM Pact High Pressure Freezer (Leica Microsystems P/N 706802) and insert it into the High Pressure Freezer.
19) Freeze the specimen using the High Pressure Freezer.
20) Transfer the Flat Specimen Pod to the Unloading Station and unscrew the Loading Device for the Flat Specimen Carrier being careful to keep it immersed in the liquid nitrogen bath.
21) Using the torque wrench, loosen the Diamond Locking Screw.
22) Using tweezers with the tips cooled in liquid nitrogen until the liquid nitrogen stops boiling, remove the Flat Specimen Carrier from the Flat Specimen Pod and place it into a small container in the liquid nitrogen bath.
23) Place the Gatan CT3500 Cryotransfer Device (Gatan Model Number CT3500) into the Gatan Specimen Workstation.
24) Fill the liquid nitrogen dewar on the Gatan CT3500 Cryotransfer device and fill the dewar on the Gatan Specimen Workstation replenishing the liquid nitrogen as necessary until rapid boiling of the liquid nitrogen stops.
25) Transfer the Flat Specimen Holder to the Gatan Specimen Workstation while keeping it in a container of liquid nitrogen.
26) Using tweezers cooled in liquid nitrogen until the liquid nitrogen stops boiling, place the flat specimen holder into the Gatan Planchette Collet (Gatan P/N PEP5099) and press down firmly.
27) Place the assembly from step 26 into the Gatan Planchette Specimen Holder (Gatan P/N PEP1395) and press down firmly.
28) Push the Gatan Cryotransfer device back into the Gatan Specimen Workstation.
29) Using the Gatan supplied 5 mm Friction Tool, screw the Gatan Planchette Specimen Holder into the Gatan Cryotransfer device.
30) Remove the Gatan Cryotransfer device from the Gatan Specimen Workstation and insert it into the Gatan Alto 2500 Cryotransfer System.
31) Attach the Gatan ITC Temperature Controller (Gatan Model Number ITC502) to the Gatan Cryotransfer device by attaching the Temperature Measurement Lead from the Gatan ITC controller to the connector on top of the Gatan Cryotransfer device.
32) Using the Gatan ITC Controller, raise the temperature of the specimen to −120° C.
33) Using the fracturing knife, break off the copper washer to fracture the specimen.
34) Reduce the temperature of the specimen below −160° C.
35) With the voltage set to 6 KV and the gas flow set to provide 10 mA sputter current, press the sputter button and once the current displays 10 mA, let the coater run for 60-90 seconds coating the specimen with gold/palladium.
36) Close the frost shield on the Gatan CT3500 Cryotransfer Device and transfer the specimen to the Hitachi S-5200 SEM/STEM.
37) Wait for the temperature of the Gatan CT3500 Cryotransfer device to stabilize, typically between −170° C. and −172° C.
38) Open the frost shield on the Gatan CT3500 Cryotransfer device by turning the frost shield control knob counterclockwise.
39) Move the sample around using the stage control trackball, locate a broken microcapsule and adjust the magnification to 50,000 to 150,000×.
40) Adjust the focus and stigmation controls to obtain the best image.
41) Acquire an image of the cross-section of the capsule wall.

Calculations

1) Select the ruler tool in the Quartz PCI software.
2) Move the cursor to one edge of the microcapsule wall.
3) Click and hold the left mouse button while dragging the mouse cursor to the opposite side of the capsule wall keeping the drawn line perpendicular to the face of the capsule wall to measure the wall thickness.
4) Use 50 independent measurements (1 measurement for each capsule) to calculate the percentage of particles having a wall thickness in the claimed range.

(4) Perfume Leakage Index is Evaluated via % Liquid-Liquid Extraction and Gas Chromatographic-Mass Spectrometric Analysis When determining the perfume leakage index from Perfume Microcapsules in liquid detergent, a fresh sample of liquid detergent with equal level of free perfume (without Perfume Microcapsules) must also be analyzed in parallel for reference.

a) Preparation of an internal standard solution:
   i. Stock solution of tonalid: Weigh 70 mg tonalid and add 20 ml hexane p.a.
   ii. Internal Standard Solution: Dilute 200 µl of stock solution in 20 ml hexane p.a.
   iii. Mix to homogenize b) Perfume extraction from liquid detergent without perfume microcapsules (reference)
   i. Weigh 2 g of liquid detergent product into an extraction vessel
   ii. Add 2 ml of Internal Standard Solution and close vessel
   iii. Extract perfume by gently turning the extraction vessel upside-down for 20 times (manually)
   iv. Add spoon tip of Sodium Sulphate
   v. After separation of layers, immediately transfer hexane-layer into Gas Chromatograph auto sampler-vial and cap vial
   vi. Inject splitless (1.5 µl) into Gas Chromatograph injection-port
   vii. Run Gas Chromatographic-Mass Spectrometric analysis c) Perfume extraction from liquid detergent with perfume microcapsules
   i. Weigh 2 g of liquid detergent product into an extraction vessel
   ii. Add 2 ml of Internal Standard Solution and close vessel
   iii. Extract perfume by gently turning the extraction vessel upside-down for 20 times (manually)
   iv. Add spoon tip of Sodium Sulphate
   v. After separation of layers, immediately transfer hexane-layer into Gas Chromatograph auto sampler-vial and cap vial
   vi. Inject splitless (1.5 µl) into Gas Chromatograph injection-port
   vii. Run Gas Chromatographic-Mass Spectrometric analysis d) Calculation
   i. The perfume leakage from capsules per individual Perfume Raw Material:

$$PerfumeLeakageIndex = \frac{\text{Area Perfume Raw Material caps} \cdot \text{Area Internal Standard Solution}_{ref} \cdot \text{Weight}_{ref}}{\text{Area Internal Standard Solution caps} \cdot \text{Area Perfume Raw Material}_{ref} \cdot \text{Weight caps}}$$

(5) Determination of Free Perfume Composition in the Slurry via % Liquid-liquid Extraction and Gas Chromatographic-Mass Spectrometric Analysis When determining the amount of free perfume composition in the microcapsule's slurry, a fresh sample in deionized water with equal level of free perfume composition (without Perfume Microcapsules) must also be analyzed in parallel for reference.

a) Preparation of an internal standard solution
   i. Stock solution of tonalid: Weigh 70 mg tonalid and add 20 ml hexane p.a.
   ii. Internal Standard Solution: Dilute 200 µl of stock solution in 20 ml hexane p.a.
   iii. Mix to homogenize b) Perfume Extraction from Deionized Water Containing Free Perfume Composition Without Perfume Microcapsules (Reference)
   i. Weigh 2 g of deionized water into an extraction vessel
   ii. Add 2 ml of Internal Standard Solution and close vessel
   iii. Extract perfume by gently turning the extraction vessel upside-down for 20 times (manually)
   iv. Add spoon tip of Sodium Sulphate
   v. After separation of layers, immediately transfer hexane-layer into Gas Chromatograph auto sampler-vial and cap vial
   vi. Inject splitless (1.5 µl) into Gas Chromatograph injection-port
   vii. Run Gas Chromatographic-Mass Spectrometric analysis c) Perfume Extraction from Liquid Detergent with Perfume Microcapsules
   i. Weigh 2 g of liquid detergent product into an extraction vessel
   ii. Add 2 ml of Internal Standard Solution and close vessel
   iii. Extract perfume by gently turning the extraction vessel upside-down for 20 times (manually)
   iv. Add spoon tip of Sodium Sulphate
   v. After separation of layers, immediately transfer hexane-layer into Gas Chromatograph auto sampler-vial and cap vial
   vi. Inject splitless (1.5 µl) into Gas Chromatograph injection-port
   vii. Run Gas Chromatographic-Mass Spectrometric analysis d) Calculation
   i. The perfume leakage from capsules per individual Perfume Raw Material:

$$PerfumeLeakageIndex = \frac{\text{Area Perfume Raw Material caps} \cdot \text{Area Internal Standard Solution}_{ref} \cdot \text{Weight}_{ref}}{\text{Area Internal Standard Solution caps} \cdot \text{Area Perfume Raw Material}_{ref} \cdot \text{Weight caps}}$$

EXAMPLES

Perfume Compositions Suitable to be Used

TABLE 1

| PRM No. | A | B | C | D | E | F | G | H | I | J | K | L |
|---|---|---|---|---|---|---|---|---|---|---|---|---|
| 1 | | | | | | | | | | | | |
| 2 | 3.5 | | | | | | | | | | | |
| 3 | 3.5 | | | | | | | | | | | 2.3 |
| 4 | | | | | | 3.6 | | | | | | |
| 5 | | | | | | | | | | | | |
| 6 | | | | | | | | | | | | |
| 7 | | | | | | | | | | | | |
| 8 | | | | | | | | | | | | |

TABLE 1-continued

| PRM No. | A | B | C | D | E | F | G | H | I | J | K | L |
|---|---|---|---|---|---|---|---|---|---|---|---|---|
| 9 | | | | | | | | | | | | |
| 10 | | | | | | | | | | | | |
| 11 | 12.5 | 3.5 | | | | | | 1.5 | | | 3.6 | |
| 12 | | | | | | | | | | | | |
| 13 | | | | | | | | | | | | |
| 14 | | | | | | | | | | | | |
| 15 | | | | | | | | | | | | |
| 16 | | | | | | | | 3.5 | | | | |
| 17 | | | | 2 | | | 2 | | | | | |
| 18 | | | | 1.8 | | | | | | 2 | | |
| 19 | | | | | | | | | | | | |
| 20 | | | | | | | | | | | | |
| 21 | | | | | | | | | | | | |
| 22 | | | | | | | | | | | 1.8 | |
| 23 | | | | | | | | | | | | |
| 24 | | | | 3.2 | | | 3.8 | | | | | |
| 25 | | | | | | | | | | | | |
| 26 | | | | | | | 13 | | | | | |
| 27 | | | | | | | | | | | | |
| 28 | | | 14 | | | | | | | | | |
| 29 | | | | | | | | | | | | |
| 30 | | | | | | | | | | | | |
| 31 | | | | 13 | | | | | | | | |
| 32 | | | 1.8 | | 3.2 | 3.5 | | | 2.3 | | | |
| 33 | | | 8.6 | | 12.5 | | | | | | | |
| 34 | | | | | | | | | | | 8.6 | |
| 35 | | | | | 4.3 | | | | | | | |
| 36 | | | | 9 | | | | | | | | |
| 37 | | | 3.5 | | | | 4 | | | | | |
| 38 | | | 1.5 | | | | | | | | | |
| 39 | | | | | | | | | | 13 | | |
| 40 | | | | | | | | | | | 12.8 | |
| 41 | | | | | | | | | | | | |
| 42 | | | | | 4 | | | | | | | |
| 43 | | | | | | 1.8 | | | | 3.8 | | |
| 44 | | | 3 | | | | | 3.6 | 2.3 | | | |
| 45 | | | 2 | | | | | | | | | |
| 46 | | | | | | | | | | | | |
| 47 | | | | | | | | | | | | |
| 48 | | | | | | | | | | | | |
| 49 | 1.8 | | | | | | | | | | 1.5 | |
| 50 | | | | | 2.3 | | | | | | 1.8 | |
| 51 | | | | | | | 2 | | | | | |
| 52 | | | | | | | | 1.7 | | | | |
| 53 | | | | | | 1.8 | | | 5 | | | |
| 54 | | | | | | | | | | | | |
| 55 | | | | | | | | | | | | |
| 56 | | | | | | | | | | | | |
| 57 | | | | | | | | | | | | |
| 58 | | | | | 4 | | | 12.5 | | | | |
| 59 | | | | | | | | | | | 2 | |
| 60 | | | | | | 5.2 | | | | | | |
| 61 | | | | | | | 5.4 | | | 5.1 | | |
| 62 | 3.5 | | | | | | | | | | 3.5 | |
| 63 | 3.5 | | | | | | | | | | | |
| 64 | 5.2 | | 3.5 | | | | | | | | | |
| 65 | | | | | | 5.3 | 9.1 | | | | | |
| 66 | 1.7 | | | | | | | 5.3 | | | 1.6 | 3.5 |
| 67 | | | | | 4 | | 3.6 | | | | | |
| 68 | | | 3.5 | | 2.4 | | | | | 3.3 | | |
| 69 | | | | 3.2 | | 3.5 | | | | | | |
| 70 | | | 1.7 | | | | | | | 1.6 | | |
| 71 | | | | | | | | | | 4 | 5.1 | |
| 72 | | | | 5 | | 1.7 | | | | | | |
| 73 | | | 3.5 | | | | | 3.5 | | | | |
| 74 | | | | | | | | 8.9 | | | | |
| 75 | | | | | | | | 1.9 | | | 3.3 | |
| 76 | 8.6 | 3.6 | | | | | | | | | | 2.4 |
| 77 | | 3.2 | | | | 3.5 | | 1.7 | | | | |
| 78 | | | | | | | | | | 5.2 | | |
| 79 | | | | | | | | 3.5 | | | 8.5 | |
| 80 | | | | | | | | | | | | |
| 81 | | | | | | 8.8 | | | | | | |
| 82 | | | 5.2 | | 5.4 | | | | | 3.5 | 5.4 | |
| 83 | | | | 2 | | | 1.6 | 3.8 | | | | |
| 84 | | 2.8 | | 5.5 | 1.3 | | | | | | | |
| 85 | | | | | | | 0.04 | | | | | |

TABLE 1-continued

| PRM No. | A | B | C | D | E | F | G | H | I | J | K | L |
|---|---|---|---|---|---|---|---|---|---|---|---|---|
| 86 | | | | | 3.2 | | | | | | | |
| 87 | 5.2 | | | | | | | | | | | 2 |
| 88 | | | | | | | 8.6 | | | | | |
| 89 | | | | | | 1.7 | | | | | | |
| 90 | | | | | | | | 0.05 | | | | |
| 91 | 1.7 | 8 | | | | | | 2 | | | | |
| 92 | | | | | | | | 5.3 | | | | |
| 93 | | | | | 1.6 | | | | | 1.8 | | |
| 94 | | | | | 5 | | 1.8 | | 2.5 | | | |
| 96 | | | | 0.04 | | 0.05 | | | | | | |
| 97 | | | 0.07 | | | | | | | 0.03 | | |
| 98 | 0.05 | | | | | | | | | | 0.05 | |
| 101 | | 7.2 | | | | | | | | | | 0.5 |
| 102 | | | | | | | | | 3.5 | | | |
| 103 | | | | | | | | | | | | |
| 104 | | | | | | | | | | | 5.5 | 3.6 |
| 105 | | 3.2 | | | 1.8 | | | | 2.3 | | | 2 |
| 107 | | 2.2 | | | 3.5 | | | | 1.8 | | | 2 |
| 109 | | | | | | | | | | | | 4 |
| 110 | | 7.8 | | | 2.3 | | | | 5.6 | | | 1.8 |
| 113 | | 1.5 | | | | | | | | | | 3.4 |
| 114 | | | 1.3 | | 1.5 | | 3.2 | | 1.2 | 1.7 | | |
| 115 | | 11.8 | | 1.4 | 3.1 | | | | 2.5 | | | 7.9 |

Example 1

Perfume Microcapsule Making

1% Poly(vinyl) alcohol solution is prepared as follows: 2 g of Poly(vinyl) Alcohol (PVA, 87-89% hydrolyzed, Mw 13,000, Sigma Aldrich) are added to 198 grams of demi-water at 50° C. and under continuous stirring. Solution is stirred till complete dissolution. Solution of 1% PVA is cooled to about 0° C. 40 grams of perfume composition A is cooled to about 0° C. Then, 3.982 grams Trimesoyl Chloride (Sigma Aldrich) are added under continuous stirring at 0° C. till Trimesoyl Chloride is completely dissolved. Then, 0.508 grams Terephthaloyl Chloride (Sigma Aldrich) are added under continuous stirring at 0° C. till complete dissolution in the perfume composition. The perfume composition containing the organic monomers at 0° C. is emulsified in the 1% PVA solution previously prepared, by slowly adding the perfume composition to the PVA solution at 1,400 rpm. The composition is emulsified during 10 minutes. Then, 8.598 grams Diethylene Triamine (Sigma Aldrich) are added to 10 grams demi-water and cooled to about 0° C. The Diethylene Triamine solution is added to the emulsified perfume composition in 5 minutes under continuous stirring at 500 rpm and at a temperature of from about 0° C. to about 3° C. A slightly increase of temperature is observed (around 2° C.). We stir the composition for 15 minutes. A Hexamethylene Diamine solution is prepared by adding 11.621 grams Hexamethylene Diamine (Sigma-Aldrich) previously melted to 10 grams of demi-water, and this solution is cooled to about 0° C. and added to previous composition in 5 minutes at 500 rpm. A slightly increase of temperature is observed (around 2° C.). Then, stirring speed is reduced to 300 rpm. After 45 minutes, an Ethylene Diamine solution is added to the composition. This solution is prepared by adding 1.503 grams Ethylene Diamine (Sigma Aldrich) to 10 grams of demi-water and it is cooled to about 0° C. Composition is stirred for 2 hours at 300 rpm till complete encapsulation is achieved. Encapsulates are centrifuged (centrifuge Jouan C3.12, Thermo Fisher Scientific), aqueous phase is removed and encapsulates are washed twice with 50 mL demi-water. Encapsulates are re-dispersed in water achieving a slurry containing 28% of perfume composition A and use directly in the consumer good.

Example 2

Perfume Microcapsule Making

1% Poly(vinyl) alcohol solution is prepared as follows: 2 g of Poly(vinyl) Alcohol (PVA, 87-89% hydrolyzed, Mw 13,000, Sigma Aldrich) are added to 198 grams of demi-water at 50° C. and under continuous stirring. Solution is stirred till complete dissolution. Solution of 1% PVA is cooled to about 0° C. 40 grams of perfume composition A is cooled to about 0° C. Then, 3.982 grams Trimesoyl Chloride (Sigma Aldrich) are added under continuous stirring at 0° C. till Trimesoyl Chloride is completely dissolved. Then, 0.508 grams Terephthaloyl Chloride (Sigma Aldrich) are added under continuous stirring at 0° C. till complete dissolution in the perfume composition. The perfume composition containing the organic monomers at 0° C. is emulsified in the 1% PVA solution previously prepared, by slowly adding the perfume composition to the PVA solution at 1,400 rpm. The composition is emulsified during 10 minutes. Then, 1,720 grams Diethylene Triamine (Sigma Aldrich) are added to 10 grams demi-water and cooled to about 0° C. The Diethylene Triamine solution is added to the emulsified perfume composition in 5 minutes under continuous stirring at 500 rpm and at a temperature of from about 0° C. to about 3° C. A slightly increase of temperature is observed (around 2° C.). We stir the composition for 15 minutes. A Hexamethylene Diamine solution is prepared by adding 14.526 grams Hexamethylene Diamine (Sigma-Aldrich) previously melted to 10 grams of demi-water, and this solution is cooled to about 0° C. and added to previous composition in 5 minutes at 500 rpm. A slightly increase of temperature is observed (around 2° C.). Then, stirring speed is reduced to 300 rpm. After 45 minutes, an Ethylene Diamine solution is added to the composition. This solution is prepared by adding 1.503 grams Ethylene Diamine (Sigma Aldrich) to 10 grams of demi-water and it is cooled to about 0° C. Composition is stirred for 2 hours at 300 rpm till complete encapsulation is achieved. Encapsulates are centrifuged (centrifuge Jouan C3.12, Thermo Fisher Scientific), aqueous phase is removed and encapsulates are washed twice with 50 mL demi-water. Encapsulates are re-dispersed in water achieving a slurry containing 25% of perfume composition A and use directly in the consumer good.

Example 3

Perfume Microcapsule Making

1% Poly(vinyl) alcohol solution is prepared as follows: 2 g of Poly(vinyl) Alcohol (PVA, 87-89% hydrolyzed, Mw 13,000, Sigma Aldrich) are added to 198 grams of demi-water at 50° C. and under continuous stirring. Solution is stirred till complete dissolution. Solution of 1% PVA is cooled to about 15° C. 40 grams of perfume composition A is cooled to about 15° C. Then, 3.982 grams Trimesoyl Chloride (Sigma Aldrich) are added under continuous stirring at 15° C. till Trimesoyl Chloride is completely dissolved. The perfume composition containing the organic monomer at 15° C. is emulsified in the 1% PVA solution previously prepared, by slowly adding the perfume composition to the PVA solution at 1,400 rpm. The composition is emulsified during 10 minutes. Then, 7,7382 grams Diethylene Triamine (Sigma Aldrich) are added to 10 grams demi-water and cooled to about 10° C. The Diethylene Triamine solution is added to the emulsified perfume composition under continuous stirring at 500 rpm and at a temperature of from about 15° C. to about 18° C. A slightly increase of temperature is observed (around 2° C.). We stir the composition for 3 hours at 300 rpm till complete encapsulation is achieved. Encapsulates are centrifuged (centrifuge Jouan C3.12, Thermo Fisher Scientific), aqueous phase is removed and encapsulates are washed twice with 50 mL demi-water. Encapsulates are re-dispersed in water and use directly in the consumer good.

Example 4

Comparative Example—Properties

Properties of capsules made following examples 1, 2 and 3 were measured and compared. Thus, it is clear that the use of specific monomer ratios and combination thereof to form the shell of the encapsulate unexpectedly improves the perfume composition's stability and, as a result, overall performance of a composition comprising the encapsulate:

| Capsules made in example ... | Mean particle size (microns)[1] | Fracture strength (MPa)[2] | Leakage (%)[3] |
|---|---|---|---|
| 1 | 26 | 2.4 | 2.6 |
| 2 | 25 | 3.2 | 2.2 |
| 3 | 23 | 1.3 | 16.4 |

[1] as described in method 3
[2] as described in method 2
[3] as described in method 4

From this table we can conclude that the use of a plurality of monomers is needed to achieve the right balance between stability in product and release during application.

Example 5

Perfume Microcapsule Making

1% Poly(vinyl) alcohol solution is prepared as follows: 2 g of Poly(vinyl) Alcohol (PVA, 87-89% hydrolyzed, Mw 13,000, Sigma Aldrich) are added to 198 grams of demi-water at 50° C. and under continuous stirring. Solution is stirred till complete dissolution. Solution of 1% PVA is cooled to about 0° C. 40 grams of perfume composition B is cooled to about 0° C. Then, 3.982 grams Trimesoyl Chloride (Sigma Aldrich) are added under continuous stirring at 0° C. till Trimesoyl Chloride is completely dissolved. Then, 1.524 grams Terephthaloyl Chloride (Sigma Aldrich) are added under continuous stirring at 0° C. till complete dissolution in the perfume composition. The perfume composition containing the organic monomers at 0° C. is emulsified in the 1% PVA solution previously prepared, by slowly adding the perfume composition to the PVA solution at 1,400 rpm. The composition is emulsified during 10 minutes. Then, 10,318 grams Diethylene Triamine (Sigma Aldrich) are added to 10 grams demi-water and cooled to about 0° C. The Diethylene Triamine solution is added to the emulsified perfume composition in 5 minutes under continuous stirring at 500 rpm and at a temperature of from about 0° C. to about 3° C. A slightly increase of temperature is observed (around 2° C.). Composition is stirred for 3 hours at 300 rpm till complete encapsulation is achieved. Encapsulates are centrifuged (centrifuge Jouan C3.12, Thermo Fisher Scientific), aqueous phase is removed and encapsulates are washed twice with 50 mL demi-water. Encapsulates are re-dispersed in water and use directly in the consumer good.

Example 6

Perfume Microcapsule Making

1% Poly(vinyl) alcohol solution is prepared as follows: 2 g of Poly(vinyl) Alcohol (PVA, 87-89% hydrolyzed, Mw 13,000, Sigma Aldrich) are added to 198 grams of demi-water at 50° C. and under continuous stirring. Solution is stirred till complete dissolution. Solution of 1% PVA is cooled to about 0° C. 40 grams of perfume composition C is cooled to about 0° C. Then, 3.982 grams Trimesoyl Chloride (Sigma Aldrich) are added under continuous stirring at 0° C. till Trimesoyl Chloride is completely dissolved. The perfume composition containing the organic monomer at 0° C. is emulsified in the 1% PVA solution previously prepared, by slowly adding the perfume composition to the PVA solution at 1,400 rpm. The composition is emulsified during 10 minutes. Then, 1,548 grams Diethylene Triamine (Sigma Aldrich) are added to 10 grams demi-water and cooled to about 0° C. The Diethylene Triamine solution is added to the emulsified perfume composition under continuous stirring at 500 rpm and at a temperature of from about 0° C. to about 3° C. A slightly increase of temperature is observed (around 2° C.). We stir the composition for 10 minutes. A Hexamethylene Diamine solution is prepared by adding 4.067 grams Hexamethylene Diamine (Sigma-Aldrich) previously melted to 10 grams of demi-water, and this solution is cooled to about 0° C. and added to previous composition at 500 rpm. A slightly increase of temperature is observed (around 2° C.). Then, stirring speed is reduced to 300 rpm. After 10 minutes, an Ethylene Diamine solution is added to the composition. This solution is prepared by adding 6.313 grams Ethylene Diamine (Sigma Aldrich) to 10 grams of demi-water and it is cooled to about 0° C. Composition is stirred for 2.5 hours at 300 rpm till complete encapsulation is achieved. Encapsulates are centrifuged (centrifuge Jouan C3.12, Thermo Fisher Scientific), aqueous phase is removed and encapsulates are washed twice with 50 mL demi-water. Encapsulates are re-dispersed in water and use directly in the consumer good.

Example 7

Perfume Microcapsule Making

1% Poly(vinyl) alcohol solution is prepared as follows: 2 g of Poly(vinyl) Alcohol (PVA, 87-89% hydrolyzed, Mw 13,000, Sigma Aldrich) are added to 198 grams of demi-water at 50° C. and under continuous stirring. Solution is stirred till complete dissolution. Solution of 1% PVA is cooled to about 0° C. 40 grams of perfume composition F is cooled to about 0° C. Then, 1.991 grams Trimesoyl Chloride (Sigma Aldrich) are added under continuous stirring at 0° C. till Trimesoyl Chloride is completely dissolved. The perfume composition containing the organic monomer at 0° C. is emulsified in the 1% PVA solution previously prepared, by slowly adding the perfume composition to the PVA solution at 1,400 rpm. The composition is emulsified during 10 minutes. Then, 3.8691 grams Diethylene Triamine (Sigma Aldrich) are added to 10 grams demi-water and cooled to about 0° C. The Diethylene Triamine solution is added to the emulsified perfume composition in 5 minutes under continuous stirring at 500 rpm and at a temperature of from about 0° C. to about 3° C. A slightly increase of temperature is observed (around 2° C.). Composition is stirred for 3 hours at 300 rpm and 0° C. till complete encapsulation is achieved. Encapsulates are centrifuged (centrifuge Jouan C3.12, Thermo Fisher Scientific), aqueous phase is removed and encapsulates are washed twice with 50 mL demi-water. Encapsulates are re-dispersed in water and use directly in the consumer good.

Example 8

Perfume Microcapsule Making

1% Poly(vinyl) alcohol solution is prepared as follows: 2 g of Poly(vinyl) Alcohol (PVA, 87-89% hydrolyzed, Mw 13,000, Sigma Aldrich) are added to 198 grams of demi-water at 50° C. and under continuous stirring. Solution is stirred till complete dissolution. Solution of 1% PVA is cooled to about 0° C. 20 grams of perfume composition J are mixed with 20 grams Isopropyl myristate (Sigma Aldrich) and then cooled to about 0° C. Then, 3.982 grams Trimesoyl Chloride (Sigma Aldrich) are added under continuous stirring at 0° C. till Trimesoyl Chloride is completely dissolved. Then, 0.508 grams Terephthaloyl Chloride (Sigma Aldrich) are added under continuous stirring at 0° C. till complete dissolution in the perfume composition. The perfume composition containing the organic monomers at 0° C. is emulsified in the 1% PVA solution previously prepared, by slowly adding the perfume composition to the PVA solution at 1,400 rpm. The composition is emulsified during 10 minutes. Then, 8.598 grams Diethylene Triamine (Sigma Aldrich) are added to 10 grams demi-water and cooled to about 0° C. The Diethylene Triamine solution is added to the emulsified perfume composition in 5 minutes under continuous stirring at 500 rpm and at a temperature of from about 0° C. to about 3° C. A slightly increase of temperature is observed (around 2° C.). We stir the composition for 15 minutes. A Hexamethylene Diamine solution is prepared by adding 11.621 grams Hexamethylene Diamine (Sigma-Aldrich) previously melted to 10 grams of demi-water, and this solution is cooled to about 0° C. and added to previous composition in 5 minutes at 500 rpm. A slightly increase of temperature is observed (around 2° C.). Then, stirring speed is reduced to 300 rpm. After 45 minutes, an Ethylene Diamine solution is added to the composition. This solution is prepared by adding 1.503 grams Ethylene Diamine (Sigma Aldrich) to 10 grams of demi-water and it is cooled to about 0° C. Composition is stirred for 2 hours at 300 rpm till complete encapsulation is achieved. Encapsulates are centrifuged (centrifuge Jouan C3.12, Thermo Fisher Scientific), aqueous phase is removed and encapsulates are washed twice with 50 mL demi-water. Encapsulates are re-dispersed in water achieving a slurry containing 14% of perfume composition J and use directly in the consumer good.

Example 9

Perfume Microcapsule Making

1% Poly(vinyl) alcohol solution is prepared as follows: 2 g of Poly(vinyl) Alcohol (PVA, 87-89% hydrolyzed, Mw 13,000, Sigma Aldrich) are added to 198 grams of demi-water at 50° C. and under continuous stirring. Solution is stirred till complete dissolution. Solution of 1% PVA is cooled to about 0° C. 30 grams of perfume composition H are mixed with 10 grams Brominated Vegetable oil (d=1.3; Virginia Dare, Brooklyn, N.Y., USA) and then cooled to about 0° C. Then, 3.982 grams Trimesoyl Chloride (Sigma Aldrich) are added under continuous stirring at 0° C. till Trimesoyl Chloride is completely dissolved. Then, 0.508 grams Terephthaloyl Chloride (Sigma Aldrich) are added under continuous stirring at 0° C. till complete dissolution in the perfume composition. The perfume composition containing the organic monomers at 0° C. is emulsified in the 1% PVA solution previously prepared, by slowly adding the perfume composition to the PVA solution at 1,400 rpm. The composition is emulsified during 10 minutes. Then, 8.598 grams Diethylene Triamine (Sigma Aldrich) are added to 10 grams demi-water and cooled to about 0° C. The Diethylene Triamine solution is added to the emulsified perfume composition in 5 minutes under continuous stirring at 500 rpm and at a temperature of from about 0° C. to about 3° C. A slightly increase of temperature is observed (around 2° C.). We stir the composition for 15 minutes. A Hexamethylene Diamine solution is prepared by adding 11.621 grams Hexamethylene Diamine (Sigma-Aldrich) previously melted to 10 grams of demi-water, and this solution is cooled to about 0° C. and added to previous composition in 5 minutes at 500 rpm. A slightly increase of temperature is observed (around 2° C.). Then, stirring speed is reduced to 300 rpm. After 45 minutes, an Ethylene Diamine solution is added to the composition. This solution is prepared by adding 1.503 grams Ethylene Diamine (Sigma Aldrich) to 10 grams of demi-water and it is cooled to about 0° C. Composition is stirred for 2 hours at 300 rpm till complete encapsulation is achieved. Encapsulates are centrifuged (centrifuge Jouan C3.12, Thermo Fisher Scientific), aqueous phase is removed and encapsulates are washed twice with 50 mL demi-water. Encapsulates are re-dispersed in water achieving a slurry containing 21% of perfume composition H and use directly in the consumer good.

Example 10-17

Examples of laundry detergent compositions comprising the perfume composition are included below.

|  | % w/w of laundry detergent compositions | | | | | | | |
|---|---|---|---|---|---|---|---|---|
| Raw material | 10 | 11 | 12 | 13 | 14 | 15 | 16 | 17 |
| Linear alkyl benzene sulphonate | 7.1 | 6.7 | 11.0 | 10.6 | 6.9 | 4.5 | 10.1 | 8.9 |
| Sodium $C_{12-15}$ alkyl ethoxy sulphate having a molar average degree of ethoxylation of 3 | 3.5 | 0.0 | 1.5 | 0.0 | 0.0 | 0.0 | 0.0 | 1.9 |
| Acrylic Acid/Maleic Acid Copolymer | 3.6 | 1.8 | 4.9 | 2.0 | 1.0 | 1.6 | 3.9 | 2.3 |
| Sodium Alumino Silicate (Zeolite 4A) | 4.0 | 0.5 | 0.8 | 1.4 | 16.3 | 0.0 | 17.9 | 2.4 |
| Sodium Tripolyphosphate | 0.0 | 17.5 | 0.0 | 15.8 | 0.0 | 23.3 | 0.0 | 0.0 |
| Sodium Carbonate | 23.2 | 16.8 | 30.2 | 17.3 | 18.4 | 9.0 | 20.8 | 30.0 |
| Sodium Sulphate | 31.4 | 29.4 | 35.5 | 7.2 | 26.3 | 42.8 | 33.2 | 28.3 |
| Sodium Silicate | 0.0 | 4.4 | 0.0 | 4.5 | 0.0 | 6.1 | 0.0 | 4.6 |
| $C_{14-15}$ alkyl ethoxylated alcohol having a molar average degree of ethoxylation of 7 | 0.4 | 2.6 | 0.8 | 2.5 | 3.1 | 0.3 | 3.8 | 0.4 |
| Sodium Percarbonate | 16.0 | 0.0 | 8.4 | 20.4 | 13.1 | 3.6 | 0.0 | 7.0 |
| Sodium Perborate | 0.0 | 9.9 | 0.0 | 0.0 | 0.0 | 0.0 | 0.0 | 0.0 |
| Tetraacetylethylenediamine (TAED) | 2.2 | 1.7 | 0.0 | 4.7 | 3.6 | 0.0 | 0.0 | 0.8 |
| Calcium Bentonite | 0.0 | 0.0 | 0.0 | 1.8 | 0.0 | 0.0 | 0.0 | 5.6 |
| Citric acid | 2.0 | 1.5 | 2.0 | 2.0 | 2.5 | 1.0 | 2.5 | 1.0 |
| Protease (84 mg active/g) | 0.14 | 0.12 | 0.0 | 0.12 | 0.09 | 0.08 | 0.10 | 0.08 |
| Amylase (22 mg active/g) | 0.10 | 0.11 | 0.0 | 0.10 | 0.10 | 0.0 | 0.14 | 0.08 |
| Lipase (11 mg active/g) | 0.70 | 0.50 | 0.0 | 0.70 | 0.50 | 0.0 | 0.0 | 0.0 |
| Cellulase (2.3 mg active/g) | 0.0 | 0.0 | 0.0 | 0.0 | 0.0 | 0.0 | 0.18 | 0.0 |
| Encapsulates of Example 1 | 2.8 | — | — | 1.8 | 0.7 | — | — | 1.2 |
| Encapsulates of Example 2 | — | 0.8 | 2.9 | — | — | 0.5 | 1.6 | — |
| Water & Miscellaneous | | | | Balance to 100% | | | | |

The equipment and materials described in Examples 6 through to 21 can be obtained from the following: IKA Werke GmbH & Co. KG, Staufen, Germany; CP Kelco, Atlanta, United States; Forberg International AS, Larvik, Norway; Degussa GmbH, Düsseldorf, Germany; Niro A/S, Soeberg, Denmark; Baker Perkins Ltd, Peterborough, United Kingdom; Nippon Shokubai, Tokyo, Japan; BASF, Ludwigshafen, Germany; Braun, Kronberg, Germany; Industrial Chemicals Limited, Thurrock, United Kingdom; Primex ehf, Siglufjordur, Iceland; ISP World Headquarters; Polysciences, Inc. of Warrington, Pa., United States; Cytec Industries Inc., New Jersey, United States; International Specialty Products, Wayne, N.J., United States; P&G Chemicals Americas, Cincinnati, Ohio, United States; Sigma-Aldrich Corp., St. Louis, Mo., United States, Dow Chemical Company of Midland, Mich., USA Examples 18-27

Fabric Conditioner

Non-limiting examples of fabric conditioners containing the polymer coated perfume microcapsules disclosed in the present specification are summarized in the following table.

|  | EXAMPLES | | | | | | | | | |
|---|---|---|---|---|---|---|---|---|---|---|
| (% wt) | 18 | 19 | 20 | 21 | 22 | 23 | 24 | 25 | 26 | 27 |
| FSA[a] | 14 | 16.47 | 14 | 12 | 12 | 16.47 | — | — | 5 | 10 |
| FSA[b] | | | | | | | 3.00 | — | — | — |
| FSA[c] | | | | | | | — | 6.5 | — | — |
| Ethanol | 2.18 | 2.57 | 2.18 | 1.95 | 1.95 | 2.57 | — | — | 0.81 | |
| Isopropyl Alcohol | — | — | — | — | — | — | 0.33 | 1.22 | — | 1.0— |
| Starch[d] | 1.25 | 1.47 | 2.00 | 1.25 | — | 2.30 | 0.5 | 0.70 | 0.71 | 0.42 |
| Phase Stabilizing Polymer[f] | 0.21 | 0.25 | 0.21 | 0.21 | 0.14 | 0.18 | 0.15 | 0.14 | 0.2 | 0.1 |
| Suds Suppressor[g] | — | — | — | — | — | — | — | 0.1 | — | — |
| Calcium Chloride | 0.15 | 0.176 | 0.15 | 0.15 | 0.30 | 0.176 | — | 0.1-0.15 | — | 0025. |
| DTPA[h] | 0.017 | 0.017 | 0.017 | 0.017 | 0.007 | 0.007 | 0.20 | — | 0.002 | 0.002 |
| Preservative (ppm)[i,j] | 5 | 5 | 5 | 5 | 5 | 5 | — | 250[j] | 5 | 5 |
| Antifoam[k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |

-continued

| (% wt) | EXAMPLES | | | | | | | | | |
|---|---|---|---|---|---|---|---|---|---|---|
| | 18 | 19 | 20 | 21 | 22 | 23 | 24 | 25 | 26 | 27 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Encapsulates as disclosed in Example 1 | 0.3 | 0.03 | 0.1 | 0.15 | 0.6 | 0.13 | 0.3 | 0.8 | 0.24 | 0.1 |
| Additional Neat Perfume | 0.8 | 0.7 | 0.9 | 0.5 | 1.2 | 0.5 | 1.1 | 0.6 | 1.0 | 0.9 |
| Deionized Water | † | † | † | † | † | † | † | † | † | † |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[f] Rheovis DCE ex BASF.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
† balance

Examples 28-30

Liquid and Gel Detergents

TABLE 1

| | (% by Weight) | | |
|---|---|---|---|
| Ingredients | 28 | 29 | 30 |
| Alkylbenzenesulfonic acid | 17.2 | 12.2 | 23 |
| C12-14 alcohol 7-ethoxylate | 8.6 | 0.4 | 19.5 |
| C14-15 alcohol 8-ethoxylate | — | 9.6 | — |
| C12-14 alcohol 3-ethoxylate sulphate, Na salt | 8.6 | — | — |
| C8-10 Alkylamidopropyldimethyl amine | — | — | 0.9 |
| Citric acid | 2.9 | 4.0 | — |
| C12-18 fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2, 5 disulfonate, Na salt | 0.9 | — | — |
| Fluorescent whitening agent | 0.3 | 0.15 | 0.3 |
| 1,2 propandiol | 3.5 | 3.3 | 22 |

TABLE 1-continued

| | (% by Weight) | | |
|---|---|---|---|
| Ingredients | 28 | 29 | 30 |
| Ethanol | — | 1.4 | — |
| Diethylene glycol | — | 1.6 | — |
| 1-ethoxypentanol | 0.9 | — | — |
| Sodium cumene sulfonate | — | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Encapsulates as Example 2 | 1.1 | 1.2 | 0.9 |
| Water | 22.1 | 50.8 | 2.9 |
| Perfume, dyes, miscellaneous minors | Balance | Balance | Balance |
| Undiluted viscosity ($V_n$) at 20 $s^{-1}$, cps | 2700 | 400 | 300 |

Example 31-33

Liquid Unit Dose

The following are examples of unit dose executions wherein the liquid composition is enclosed within a PVA film. The preferred film used in the present examples is Monosol M8630 76 μm thickness.

| | 31 D 3 compartments | | | 32 E 2 compartments | | 33 F 3 compartments | | |
|---|---|---|---|---|---|---|---|---|
| Compartment # | A | B | C | D | E | F | G | H |
| Dosage (g) | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |

-continued

| Ingredient | | | | | | | | |
|---|---|---|---|---|---|---|---|---|
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| Enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | | 0.4 | | |
| Brightener | 0.2 | 0.2 | 0.2 | 0.3 | | 0.3 | | |
| Encapsulates as Example2 | 0.4 | 1.2 | 1.5 | 1.3 | — | 0.8 | — | — |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . . ) | 2.0 | 2.0 | 2.0 | 4.0 | 1.5 | 2.2 | 2.2 | 2.0 |
| Buffers (sodium carbonate, monoethanolamine)[3] | To pH 8.0 for liquids / To RA > 5.0 for powders | | | | | | | |
| Solvents (1,2 propanediol, ethanol), Sulfate | To 100p | | | | | | | |

[1]Polyethylenimine (MW = 600) with 20 ethoxylate groups per —NH.
[3]RA = Reserve Alkalinity (g NaOH/dose)

Example 34-37

Liquid Laundry Detergent

| | Liquid Detergent Compositions | | | |
|---|---|---|---|---|
| Ingredient | 34 (Comparative) % | 35 (Invention) % | 36 (Invention) % | 37 (Invention) % |
| Linear Alkylbenzene sulfonic acid[1] | 15 | 15 | 12 | 12 |
| C12-14 alkyl ethoxy 3 sulfate MEA salt | 10 | 10 | 8 | 9 |
| C12-14 alkyl 7-ethoxylate | 10 | 10 | 8 | 8 |
| C14-15 alkyl 8-ethoxylate | — | — | — | — |
| C12-18 Fatty acid | 10 | 10 | 10 | 10 |
| Citric acid | 2 | 2 | 3 | 3 |
| Ethoxysulfated Hexamethylene Diamine Dimethyl Quat | — | — | — | 2.2 |
| Soil Suspending Alkoxylated Polyalkylenimine Polymer[2] | 3 | 3 | 2.2 | — |
| PEG-PVAc Polymer[3] | — | — | 0.9 | 0.9 |
| Hydroxyethane diphosphonic acid | 1.6 | 1.6 | 1.6 | 1.6 |
| Fluorescent Whitening Agent | 0.2 | 0.2 | 0.2 | 0.2 |
| 1,2 Propanediol | 6.2 | 6.2 | 8.5 | 8.5 |
| Ethanol | 1.5 | 1.5 | — | — |
| Hydrogenated castor oil derivative structurant | 0.75 (introduced via NaLAS premix) | (introduced via MEA LAS premix) | 0.75 | |
| Boric acid | 0.5 | 0.5 | 0.5 | 0.5 |
| Perfume | 1.7 | 1.7 | 1.7 | 1.7 |
| Encapsulates as Example 1 | 1.1 | 1.2 | 0.9 | 1.3 |
| Monoethanolamine | To pH 8.0 | | | |
| Protease enzyme | 1.5 | 1.5 | 1.5 | 1.5 |
| Amylase enzyme | 0.1 | 0.1 | 0.1 | 0.1 |
| Mannanase enzyme | 0.1 | 0.1 | 0.1 | 0.1 |
| Cellulase enzyme | — | — | 0.1 | 0.1 |
| Xyloglucanase enzyme | — | — | 0.1 | 0.1 |

-continued

Liquid Detergent Compositions

| Ingredient | 34 (Comparative) % | 35 (Invention) % | 36 (Invention) % | 37 (Invention) % |
|---|---|---|---|---|
| Pectate lyase | — | — | 0.1 | 0.1 |
| Water and minors (antifoam, aesthetics, . . . ) | | To 100 parts | | |

[1] Weight percentage of Linear Alkylbenzene sulfonic acid includes that which added to the composition via the premix
[2] 600 g/mol molecular weight polyethylenimine core with 20 ethoxylate groups per —NH.
[3] PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

Example 38

Shampoo Formulation

| Ingredient | |
|---|---|
| Ammonium Laureth Sulfate ($AE_3S$) | 6.00 |
| Ammonium Lauryl Sulfate (ALS) | 10.00 |
| Laureth-4 Alcohol | 0.90 |
| Trihydroxystearin[7] | 0.10 |
| Encapsulates as disclosed in Example 1 | 0.60 |
| Sodium Chloride | 0.40 |
| Citric Acid | 0.04 |
| Sodium Citrate | 0.40 |
| Sodium Benzoate | 0.25 |
| Ethylene Diamine Tetra Acetic Acid | 0.10 |
| Dimethicone[9, 10, 11] | 1.00[9] |
| Water and Minors (QS to 100%) | Balance |

Examples 39-41

Hard Surface Cleaner Bathroom Composition

| % Weight | 39 | 40 | 41 |
|---|---|---|---|
| C9-C11 EO8 (Neodol 91-8 ®) | 3 | 2.5 | 3.5 |
| Alkyl Benzene sulfonate | | 1 | |
| C12-14-dimethyl Aminoxide | | 1 | |
| n-Butoxy Propoxy Propanol | | 2 | 2.5 |
| Hydrogene Peroxide | 3 | | |
| Hydrophobic ethoxylated polyurethane (Acusol 882 ®) | 1.5 | 1 | 0.8 |
| Lactic Acid | 3 | | 3.5 |
| Citric Acid | | 3 | 0.5 |
| Polysaccharide (Xanthan Gum, Keltrol CG-SFT ® Kelco) | 0.25 | 0.25 | 0.25 |
| Perfume | 0.35 | 0.35 | 0.35 |
| Encapsulates as disclosed in Example 1 | 2.0 | 0.7 | 3.5 |
| Water | Balance | Balance | Balance |

Example 42-44

Hard Surface Cleaner Bathroom Composition (Cont.)

| % Weight | 42 | 43 | 44 |
|---|---|---|---|
| Chloridric acid | 2 | | |
| Linear C10 alkyl sulphate | 1.3 | 2 | 3 |
| n-Butoxy Propoxy Propanol | 2 | | 1.75 |
| Citric Acid | | 3 | 3 |
| PolyvinylPyrrolidone (Luviskol K60 ®) | 0.1 | 0.1 | 0.1 |
| NaOH | | 0.2 | 0.2 |
| Perfume | 0.4 | 0.4 | 0.4 |
| Polysaccharide (Xanthan Gum Kelzan T ®, Kelco) | 0.3 | 0.35 | 0.35 |
| Encapsulates as disclosed in Example 2 | 1.8 | 2.9 | 0.9 |
| Water | Balance | Balance | Balance |

Examples 45-47

Hand-Dishwashing Detergent Compositions

| % Weight | 45 | 46 | 47 |
|---|---|---|---|
| N-2-ethylhexyl sulfocuccinamate | 3 | 3 | 3 |
| C11EO5 | 7 | 14 | |
| C11-EO7 | | | 7 |
| C10-EO7 | 7 | | 7 |
| Trisodium Citrate | 1 | 1 | 1 |
| Potassium Carbonate | 0.2 | 0.2 | 0.2 |
| Perfume | 1 | 1 | 1 |
| Polysaccharide (Xanthan Gum Kelzan T ®, Kelco) | 0.35 | 0.35 | 0.35 |
| Encapsulates as disclosed in Example 1 | 0.3 | 0.1 | 0.05 |
| Water (+minor e.g.; pH adjusted to 10.5) | Balance | Balance | Balance |

Examples 48-49

General Degreaser Composition

| % Weight | 48 | 49 |
|---|---|---|
| C9-C11 EO8 (Neodol 91-8 ®) | 3 | 3 |
| N-Butoxy Propoxy Propanol | 15 | 15 |
| Ethanol | 10 | 5 |

-continued

| % Weight | 48 | 49 |
|---|---|---|
| Isopropanol | | 10 |
| Polysaccharide (Xanthan Gum-glyoxal modifiedOptixan-T) | 0.35 | 0.35 |
| Encapsulates as disclosed in Example 1 | 1.6 | 0.8 |
| Water (+minor e.g.; pH adjusted to alkaline pH) | Balance | Balance |

Examples 50-52

Scouring Composition

| % Weight | 50 | 51 | 52 |
|---|---|---|---|
| Sodium C13-16 paraffin sulfonate | 2.5 | 2.5 | 2.5 |
| C12-14-EO7 (Lutensol AO7 ®) | 0.5 | 0.5 | 0.5 |
| Coconut Fatty Acid | 0.3 | 0.3 | 0.3 |
| Sodium Citrate | 3.3 | 3.3 | 3.3 |
| Sodium Carbonate | 3 | 3 | 3 |
| Orange terpenes | 2.1 | 2.1 | 2.1 |
| Benzyl Alcohol | 1.5 | 1.5 | |
| Polyacrylic acid 1.5 Mw | 0.75 | 0.75 | 0.75 |
| Diatomaceous earth (Celite 499 ® median size 10 μm) | 25 | | |
| Calcium Carbonate (Merk 2066 ® median size 10 μm) | | 25 | |
| Encapsulates as disclosed in Example 1 | 4.0 | 2.5 | 1.2 |
| Water | Balance | Balance | Balance |

Examples 53-54

Liquid Glass Cleaner

| % Weight | 53 | 54 |
|---|---|---|
| Butoxypropanol | 2 | 4 |
| Ethanol | 3 | 6 |
| C12-14 sodium sulphate | 0.24 | |
| NaOH/Citric acid | To pH 10 | |
| Citric Acid | | |
| Encapsulates as disclosed in Example 2 | 1.0 | 0.5 |
| Water (+minor) | Balance | Balance |

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A population of encapsulates, at least 80% of the encapsulates comprising a shell and a core, said shell comprising a polyamide polymer that forms a wall that encapsulates said core, said core comprising a perfume composition, said perfume composition comprising perfume raw materials having a ClogP of from 2.0 to 4.5, said encapsulate having a diameter of from 1 μm to 100 μm, said encapsulate having a fracture strength from 0.1 MPa to 5 MPa, wherein the polyamide polymer comprises three or more water miscible monomers, wherein the polyamide polymer comprises two or more water immiscible organic monomers, wherein the water miscible monomer comprises diethylene triamine, hexamethylene diamine and ethylene diamine, and wherein the water immiscible organic monomer is selected from the group consisting of diacyl chlorides, triacyl chlorides and mixtures thereof.

2. The population of encapsulates according to claim 1 wherein said encapsulates' core comprises a perfume composition selected from the group consisting of:
   a) a perfume composition having a ClogP of less than 4.5 to 2;
   b) a perfume composition comprising, based on total perfume composition weight, at least 60% perfume materials having a ClogP of less than 4.0 to 2;
   c) a perfume composition comprising, based on total perfume composition weight, at least 35% perfume materials having a ClogP of less than 3.5 to 2;
   d) a perfume composition comprising, based on total perfume composition weight, at least 40% perfume materials having a ClogP of less than 4.0 to 2 and at least 1% perfume materials having a ClogP of less than 2.0 to 1;
   e) a perfume composition comprising, based on total perfume composition weight, at least 40% perfume materials having a ClogP of less than 4.0 to 2 and at least 15% perfume materials having a ClogP of less than 3.0 to 1.5;
   a perfume composition comprising, based on total perfume composition weight, at least 1% of a butanoate ester and at least 1% of a pentanoate ester;
   g) a perfume composition comprising, based on total perfume composition weight, at least 2% of an ester comprising an allyl moiety and at least 10% of another perfume comprising an ester moiety;
   h) a perfume composition comprising, based on total perfume composition weight, at least 1% of an aldehyde comprising an alkyl chain moiety;
   i) a perfume composition comprising, based on total perfume composition weight, at least 2% of a butanoate ester;
   j) a perfume composition comprising, based on total perfume composition weight, at least 1% of a pentanoate ester;
   k) a perfume composition comprising, based on total perfume composition weight, at least 3% of an ester comprising an allyl moiety and at least 1% of an aldehyde comprising an alkyl chain moiety;
   l) a perfume composition comprising, based on total perfume composition weight, at least 25% of a perfume comprising an ester moiety and at least 1% of an aldehyde comprising an alkyl chain moiety: and m) a perfume composition comprising, based on total perfume composition weight, from 0.5% to 50% of a parametric balancing agent, with the proviso that the perfume composition does not contain alcohols and/or primary amine perfume raw materials.

3. The population of encapsulates according claim 1, said encapsulates having a leakage index of from 0 to 0.35.

4. The population of encapsulates according claim 1 said encapsulates having a core to shell mass ratio of from 75:25 to 95:5.

5. A consumer product comprising, based on total consumer product weight, from 0.01% to 80% of the population of encapsulates according to claim 1.

6. The consumer product according to claim 5, wherein at least 75% of said encapsulates have a capsule wall thickness of from 50 nm to 500 nm.

7. The consumer product according to claim 5 wherein for said population of encapsulates, said encapsulates have a percentage of free perfume composition of less than 10%.

8. A method of treating and/or cleaning a situs, said method comprising
 a) optionally washing and/or rinsing said situs;
 b) contacting said situs with a population of encapsulates according to claim 1; and
 c) optionally washing and/or rinsing said situs.

9. A process of making a consumer product according to claim 5, comprising combining a consumer product adjunct material and a population of encapsulates according to claim 1.

10. A process according to claim 9 wherein said population of encapsulates is made by:
 a) combining a second solution and a second composition to form a third composition, said second solution comprising based on total weight from 10% to 90% water, and water miscible monomer comprises diethylene triamine, hexamethylene diamine and ethylene diamine, said second composition being made by combining, at temperature of from 0° C. to 25° C., a first composition and a first solution and emulsifying said combination of said first composition and said first solution,
  (i) said first composition being made by combining based on total first composition weight, from 65% to 97% core material, and a water immiscible organic monomer selected from the group consisting of dichlorides, triacyl chlorides and mixtures thereof, preferably, said dichlorides may be selected from the group consisting of sebacoyl dichloride, adipoyl dichloride, and mixtures thereof and said triacyl chlorides may be selected from the group consisting of teraphthaloyl chloride, trimesoyl chloride, acetyl chloride, benzoyl chloride, 1,3,5-benzentricarbonyl chloride, and mixtures thereof and cooling said first composition, said core material comprising a perfume composition, said perfume composition comprising perfume raw materials having a ClogP of from 2.0 to 4.5;
  (ii) said first solution comprising, based on total first solution weight, from 0.1% to 5%, of an emulsifier;
 b) stirring said third composition for at least 15 minutes at a temperature of from 0° C. to 25° C.

11. The population of encapsulates according to claim 1, wherein said diacyl chlorides are selected from the group consisting of sebacoyl dichloride, adipoyl dichloride, and mixtures thereof, and wherein said triacyl chlorides are selected from the group consisting of teraphthaloyl chloride, trimesoyl chloride, acetyl chloride, benzoyl chloride, 1,3,5-benzentricarbonyl chloride, and mixtures thereof.

12. The population of encapsulates according to claim 1, wherein said polyamide polymer comprises three water miscible monomers, and wherein said polyamide polymer comprises two water immiscible organic monomers.

13. The population of encapsulates according to claim 12, wherein said three water miscible monomers are diethylene triamine, hexamethylene diamine, and ethylene diamine, and wherein said two water immiscible organic monomers are teraphthaloyl chloride and trimesoyl chloride.

\* \* \* \* \*